US012667424B2

(12) United States Patent
Signoretti et al.

(10) Patent No.: US 12,667,424 B2
(45) Date of Patent: Jun. 30, 2026

(54) TOOL FOR INSERTING AN IMPLANT AND METHOD OF USING SAME

(71) Applicant: Waldemar Link GmbH & Co. KG, Hamburg (DE)

(72) Inventors: Riccardo Signoretti, Jersey City, NJ (US); Louis-Francois Lapointe, Livingston, NJ (US); Jennifer Gass, Summit, NJ (US); Obinna Nwanna, Morristown, NJ (US); Raymond Bellon, Jersey City, NJ (US)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 1152 days.

(21) Appl. No.: 17/513,469

(22) Filed: Oct. 28, 2021

(65) Prior Publication Data

US 2022/0125518 A1 Apr. 28, 2022

Related U.S. Application Data

(60) Provisional application No. 63/106,873, filed on Oct. 28, 2020.

(51) Int. Cl.
*A61B 34/10* (2016.01)
*A61B 34/20* (2016.01)

(52) U.S. Cl.
CPC .............. *A61B 34/10* (2016.02); *A61B 34/20* (2016.02); *A61B 2034/104* (2016.02); *A61B 2034/107* (2016.02)

(58) Field of Classification Search
CPC .......... A61B 17/56; A61B 34/10; A61B 34/20
See application file for complete search history.

(56) References Cited

U.S. PATENT DOCUMENTS

| | | | | |
|---|---|---|---|---|
| 6,126,670 | A | * 10/2000 | Walker | ................. A61B 17/142 173/217 |
| 2009/0270864 | A1* | 10/2009 | Poncet | ..................... A61F 2/40 606/83 |
| 2014/0200439 | A1 | 7/2014 | Barsoum et al. | |

(Continued)

FOREIGN PATENT DOCUMENTS

| | | | |
|---|---|---|---|
| EP | 2719353 A1 | 4/2014 | |
| EP | 2901957 A1 | 8/2015 | |

OTHER PUBLICATIONS

LimaCorporate. "LimaCorporate_Smart Space." YouTube.com, Feb. 4, 2021, 1 page, [Online] [Retrieved Apr. 11, 2022], Retrieved from the Internet <URL:https://www.youtube.com/watch?v=N-x7wXXlqBE>.

(Continued)

*Primary Examiner* — Bijan Mapar
(74) *Attorney, Agent, or Firm* — Chiesa Shahinian & Giantomasi PC

(57) ABSTRACT

An implant insertion tool or tools interact with a user interface provided by a computer to guide the operator to insert the implant at a desired location and trajectory. The user interface may guide an operator through a registration process, a process for positioning the tip of the implant at the desired location, and a process for aligning the implant to have the desired insertion trajectory. The implant may be a medical implant such as a K-wire that is inserted into a bone, such as the glenoid of a scapula during shoulder arthroplasty or reverse arthroplasty.

15 Claims, 17 Drawing Sheets

(56) References Cited

U.S. PATENT DOCUMENTS

| | | | | |
|---|---|---|---|---|
| 2014/0232316 A1* | 8/2014 | Philipp | .................. | B01F 35/90 |
| | | | | 318/504 |
| 2017/0354426 A1* | 12/2017 | Glard | .................... | A61B 90/10 |
| 2019/0380789 A1* | 12/2019 | Link | ..................... | A61B 34/20 |

OTHER PUBLICATIONS

PCT International Search Report and Written Opinion, PCT Application No. PCT/IB2021/059997, Mar. 28, 2022, 21 pages.
PCT Invitation to Pay Additional Fees, PCT Application No. PCT/IB2021/059997, Feb. 7, 2022, 14 pages.

* cited by examiner

INCLINATION
7.5°
7°
Planned

VERSION
8.0°
8°
Planned 0.5°
TO TARGET

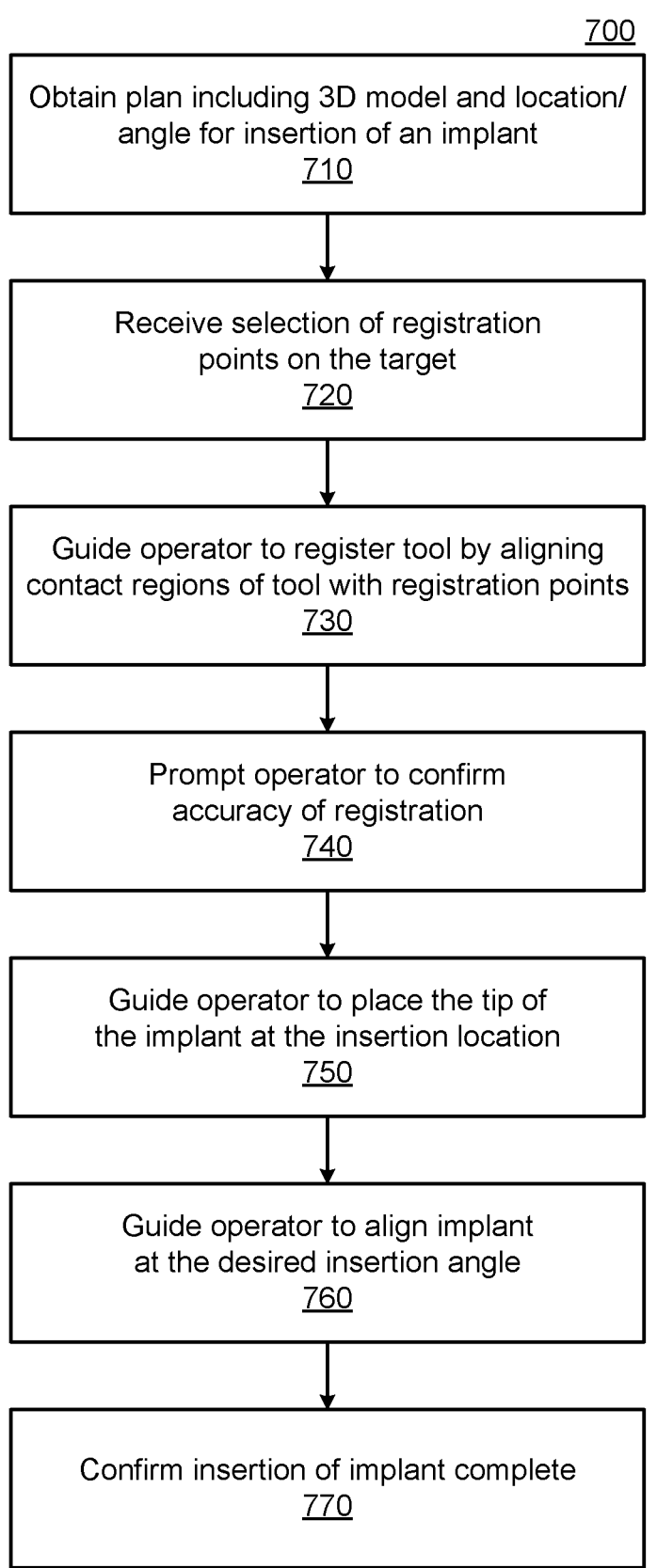

700

Obtain plan including 3D model and location/
angle for insertion of an implant
710

Receive selection of registration
points on the target
720

Guide operator to register tool by aligning
contact regions of tool with registration points
730

Prompt operator to confirm
accuracy of registration
740

Guide operator to place the tip of
the implant at the insertion location
750

Guide operator to align implant
at the desired insertion angle
760

Confirm insertion of implant complete
770

Identify registration points on the target
810

Align contact regions of tool
with registration points
820

Verify accuracy of registration
830

Place the tip of the implant at
the marked insertion location
840

Align implant at the indicated angle
850

Insert implant
860

TOOL FOR INSERTING AN IMPLANT AND METHOD OF USING SAME

CROSS REFERENCE TO RELATED APPLICATIONS

This application claims the benefit of U.S. Provisional Application No. 63/106,873, filed Oct. 28, 2020, which is incorporated by reference.

BACKGROUND

1. Technical Field

The subject matter described relates generally to computer-navigated tools and, in particular, to a surgical tool for guided insertion of an implant.

2. Background Information

Shoulder arthroplasty is a technically demanding procedure, with complications most often arising in association with the glenoid component. Correct implant positioning in terms of version and inclination may be challenging due to a variety of issues related to patient anatomy and surgical technique. Altered anatomy in revision cases, glenoid bone loss, and unreliable landmarks are commonly encountered problems. In these cases, directing the glenoid baseplate along an appropriate axis with sufficient bone stock may be a difficult intra-operative task. Three-dimensional (3D) reconstructions of computed tomography (CT) or magnetic resonance imaging (MRI) scans can improve surgical planning, but recreating the same plan during surgery can be a demanding task.

SUMMARY

An implant insertion tool or tools interact with a user interface provided by a computer to guide the operator to insert the implant into a surface at a desired location and trajectory. The implant may be a medical implant such as a Kirschner-wire (K-wire), Steinmann pin, guide wire, alignment pin, central pin, guide pin, baseplate, glenoid component, glenoid implant, or the like that is inserted into a bone, such as the glenoid of a scapula during shoulder arthroplasty or reverse arthroplasty. Embodiments of the tool and process may also be used to insert implants into surfaces other than bone.

In one embodiment, the tool includes a body, a sensor unit configured to generate position data indicating a position of the body, and a probe. The position data may indicate translation position (also referred to as location), angular position, acceleration, angular rate, or some combination thereof, which may be processed (possibly in conjunction with other information) to determine a position of the tool relative to the surface. The probe includes an attachment portion and a head. The attachment portion attaches the probe to the body. The head is coupled to the attachment portion (e.g., via a shaft) and has a plurality of contact portions configured to contact the target surface. The tool also includes a controller configured to send the position data to a computer. The computer may provide assistance to a user in positioning the tool to insert the implant at the desired location and angle.

In another embodiment, a non-transitory computer-readable medium stores instructions for assisting a user to insert the implant in the surface at the desired location and trajectory using the tool. The instructions may be executed by a computer to cause the computer to access a 3D model of the surface and annotate the 3D model of the surface with registration points. The registration points correspond to contact portions of the tool. The instructions further cause the computer to provide a graphical user interface for display to the operator to guide the operator to align the contact portions of the tool with the registration points, thus registering the tool. The graphical user interface is updated to display location targeting information that guides the user to position a tip of the implant at the desired location on the surface. The graphical user interface is further updated to display angle targeting information that guides the user to align the implant with the desired angle.

In a further embodiment, a method for inserting an implant in a surface using a tool and aided by a computer-based user interface includes identifying registration points on the surface. The registration points are indicated on a 3D model of the surface displayed in the user interface. The method further includes aligning contact regions of the tool with the registration points to establish a registration between the tool and a 3D model. The implant is positioned using information displayed in the user interface that is determined using the established registration and the implant is inserted.

BRIEF DESCRIPTION OF THE DRAWINGS

FIG. 7 is a flowchart of an example computer-implemented method for guiding the insertion of an implant with the tool, according to one embodiment.

DETAILED DESCRIPTION

The Figures (FIGS.) and the following description describe certain embodiments by way of illustration only. One skilled in the art will readily recognize from the following description that alternative embodiments of the structures and methods may be employed without departing from the principles described. Wherever practicable, similar or like reference numbers are used in the figures to indicate similar or like functionality. Where elements share a common numeral followed by a different letter, this indicates the elements are similar or identical. A reference to the numeral alone generally refers to any one or any combination of such elements, unless the context indicates otherwise.

Overview

A surgeon may develop a surgical plan using a 3D model. For example, in the case of shoulder arthroplasty, the surgeon may identify an entry location on the glenoid and a trajectory for anchoring a surgical implant (e.g., a K-wire, Steinmann pin, guide wire, alignment pin, central pin, guide pin, baseplate, glenoid component, glenoid implant, etc.) in the scapula. Computer-aided navigation may then be used during surgery to execute the surgical plan. However, existing computer-assisted implantation techniques use a tracking system that is physically distinct from the implantation tool. These techniques have several disadvantages, including cumbersome instrumentation, the potential for iatrogenic lesions from fixation pins, time-consuming landmark registration, and increased operative time. The tracking devices may also loosen during surgery, resulting in unreliable information.

Another class of solutions use patient-specific instrumentation (PSI). PSI has become popular in orthopedic subspecialties such as total hip and knee arthroplasty, pelvic and acetabular procedures, and spinal deformities, with varying degrees of success. While these techniques are effective in placement of implants for both anatomical and reverse shoulder arthroplasties, there are several disadvantages. These disadvantages include requiring a lead time of two or more weeks to receive the instrument before surgery and the missed opportunity to collect data during the surgery. Furthermore, approaches using PSI generally lack real-time feedback during surgery and it may be difficult or impossible for the surgeon to compensate for any discrepancies if the PSI does not accurately match the anatomy of the patient.

Various embodiments of the disclosed surgical tool and method combine the advantages of both types of solution while addressing one or more of the disadvantages. The surgical tool may be immediately ready for use upon completion of a surgical plan, be used without a marker, provide rapid registration between the 3D model and the physical position and orientation of the surgical tool, enable real time feedback, and/or allow for data collection during surgery.

Figure 1:
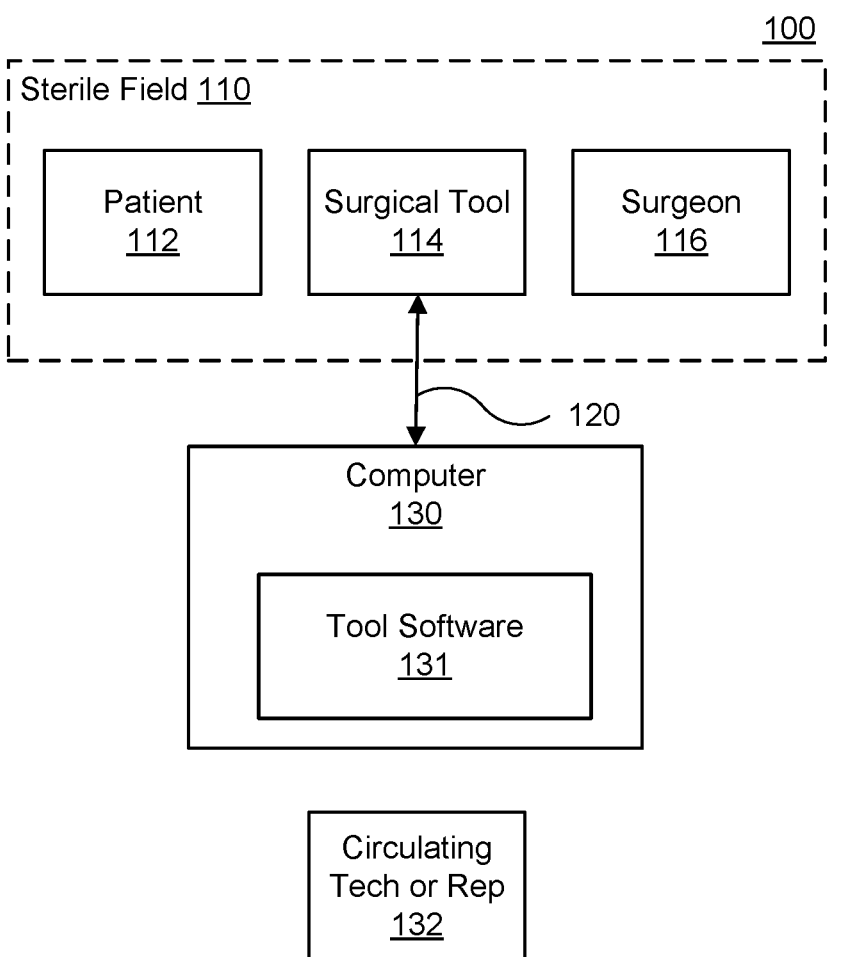
FIG. 1 is a block diagram of a surgical environment 100 including an implant insertion tool with computer-aided navigation, according to one embodiment.

FIG. 1 illustrates one embodiment of a surgical environment 100. In the embodiment shown, the surgical environment 100 includes a patient 112, a surgical tool 114, and a surgeon 116 within a sterile field 110. The surgical environment 100 also includes a computer 130 overseen by a circulating technician or representative 132 that are outside of the sterile field 110. Alternatively, the computer 130 may be located and operated by a medical professional within the sterile field 100. In either case, the computer 130 is connected to the surgical tool 114 via a communications channel 120 (e.g., a Bluetooth® connection, a local area network (LAN) or the internet). In other embodiments, the surgical environment 100 includes different and/or additional elements. In addition, the functions may be distributed among the elements in a different manner than described.

The surgeon 116 uses the surgical tool 114 to insert an implant in the patient 112. For illustrative purposes, various embodiments are described in which the implant is a K-wire being anchored in the patient's glenoid as part of shoulder arthroplasty or reverse shoulder arthroplasty. However, one of skill in the art will recognize that similar techniques may be used for a range of other surgeries. Furthermore, the disclosed registration, target selection, and alignment process may be used in other contexts where it is desirable to insert an implant at a particular location and with a specified trajectory with precision and accuracy. Thus, while the term surgeon 116 is used to refer to the operator of the tool for convenience, in some embodiments, the tool may be operated by someone other than a surgeon. These additional use cases should be considered as within the scope of this disclosure unless it is apparent from the context that a particular technique is limited to a specific context or set of contexts.

The surgical tool 114 includes one or more sensors that generate position data describing the orientation, location, and/or acceleration of the surgical tool. The surgical tool 114 sends the position data to the computer 130 (e.g., via the communications channel 120). In one embodiment, the sensors generate acceleration data and angular rate data. These data are processed to estimate the orientation of the surgical tool 114. These data may also be double integrated to generate an estimate of the surgical tool's position. Regardless of the specific type or types of data generated by the sensors, the computer 130 executes tool software 131 that provides for display of a user interface to guide the surgeon 116 through a registration process. The registration process generates mappings between the surgical plan's 3D model and the coordinate system of the sensors in the surgical tool 114. Once the surgical tool 114 is registered, the user interface may guide the surgeon 116 to place the tip of an implant at the planned entry location and/or orient the implant for insertion at the planned trajectory.

Example Surgical Tools

FIGS. 2A through 2D illustrate the body of an example surgical tool 114 that may operate with computer-aided navigation for insertion of an implant, according to one embodiment. In the embodiment shown, the body includes a sensor unit 210 and a power unit 220. The sensor unit 210 and the power unit 220 are coupled during use to collectively form the body of the surgical tool 114. A probe is coupled to the body (e.g., to the sensor unit 210) during operation. Various embodiments of probe are described in greater detail below, with reference to FIG. 3. After use, the sensor unit 210 may be decoupled from the probe/power unit 220 and sterilized (e.g., using an autoclave) for use in another surgery. The probe may be similarly sterilized for reuse. The power unit 220 may be single use and disposed of after the surgery is completed. In other embodiments, the sensor unit 210 and power unit 220 may be combined into a single housing or split into three or more distinct units that are connected together when used. Furthermore, the components may be distributed between the units in different manners than shown and described.

Figure 2A:
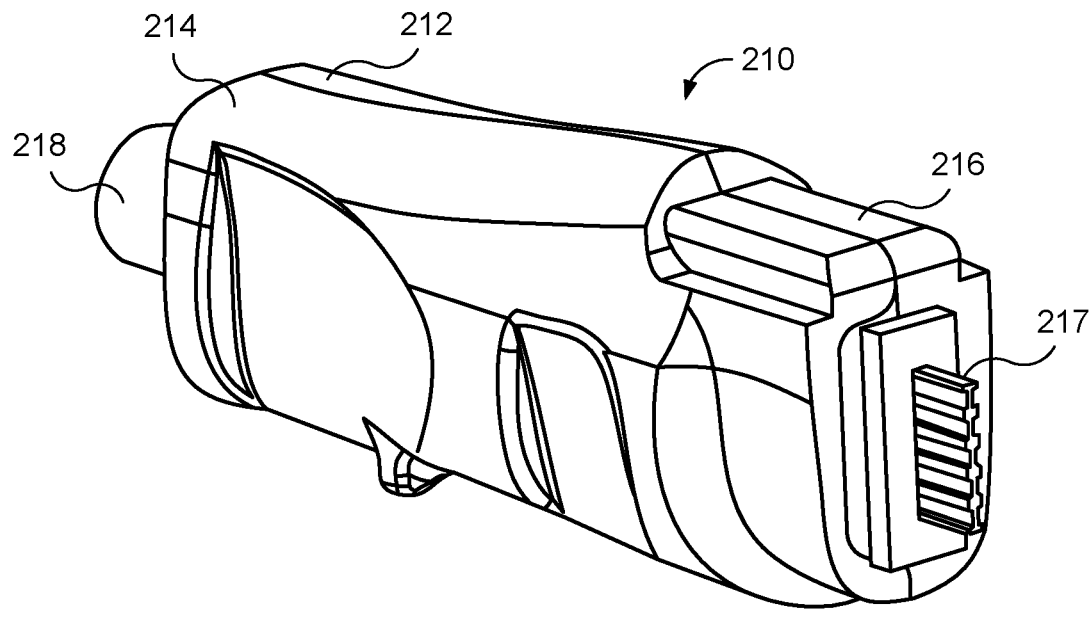
FIG. 2A is a perspective view of a sensor unit of the tool, according to one embodiment.

FIG. 2A illustrates one embodiment of the sensor unit 210 of the surgical tool 114. In the embodiment shown, the sensor unit 210 has a housing formed from a first piece 212 and a second piece 214. The sensor housing pieces may be clipped, glued, or otherwise connected together to form an enclosure. A first end of the sensor housing has a physical connector 216 that engages with a corresponding connector 228 of the power unit 220. For example, the connector 216 may include flanges, slots, clips, and/or the like for securely connecting the sensor unit 210 to the power unit 220. An electrical connector 217 is located at the first end of the sensor housing. The electrical connector 217 engages with a corresponding electrical connector 229 on the power unit 220 to enable the power unit 220 to provide electrical power to components of the sensor unit 210. The electrical connector 217 may also enable data and/or other electrical signals to be exchanged between the sensor unit 210 and the power unit 220. A mount 218 for physically connecting a probe to the sensor unit 210 is located at a second end of the sensor housing (e.g., opposite the first end).

Figure 2B:
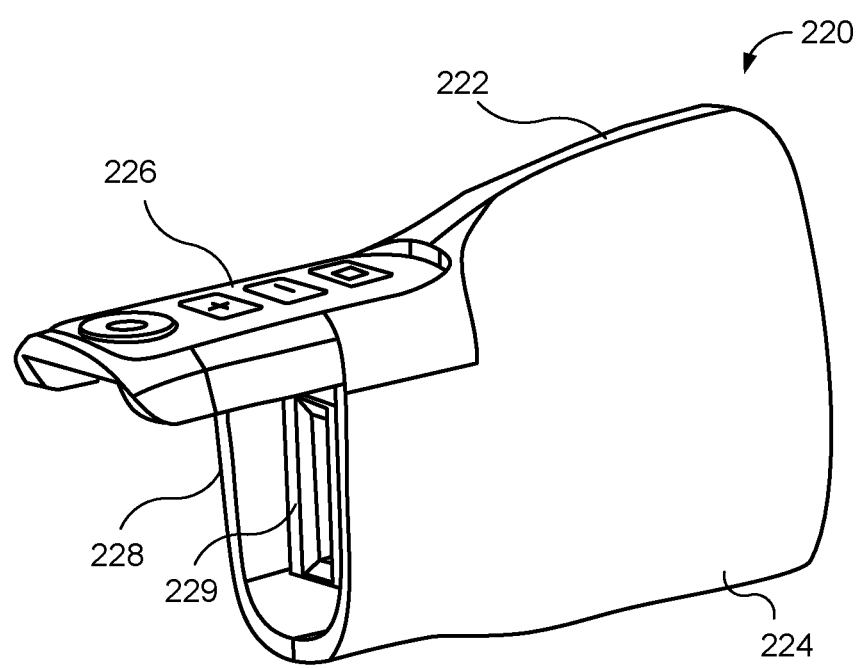
FIG. 2B is a perspective view of a power unit of the tool, according to one embodiment.

FIG. 2B illustrates one embodiment of the power unit 220. In the embodiment shown, the power unit 220 has a housing formed from a first piece 222 and a second piece 224. The power unit housing pieces may be clipped, glued, or otherwise connected together to form an enclosure. The power unit 220 has one or more controls 226 on an exterior surface of the housing. For example, the controls 226 may include one or more buttons (e.g., membrane switches) for receiving input from the surgeon 116 and/or one or more indicators (e.g., LEDs) for conveying information to the surgeon. The physical connector 228 that engages with the sensor unit 210 is located at one end of the power unit 220. The electrical connector 229 that engages with the electrical connector 217 of the sensor unit is also located at the same end of the power unit 220.

Figure 2C:
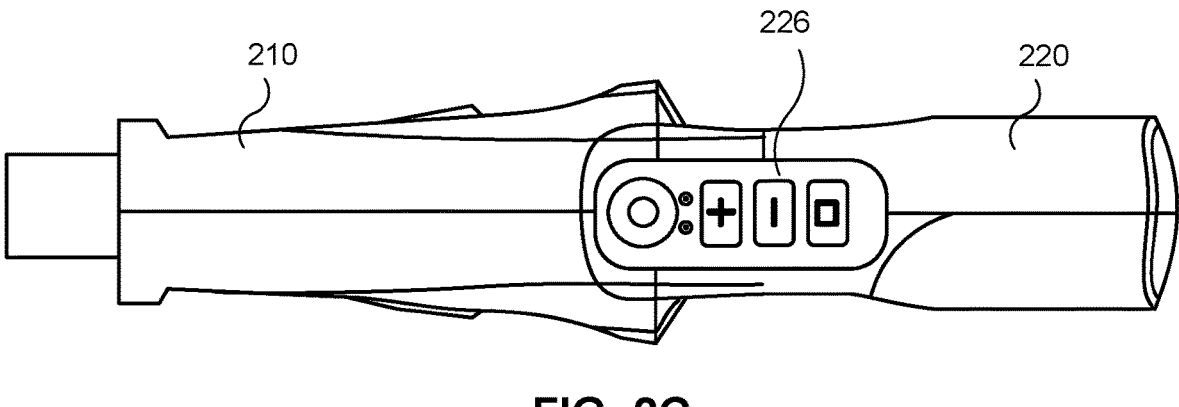
FIG. 2C is a top view of the sensor unit and the power unit of the tool when connected with each other, according to one embodiment.

FIG. 2C illustrates the sensor unit 210 and the power unit 220 connected together forming the body of the surgical tool 114, according to one embodiment. The surgeon 116 may grip the body of the surgical tool 114 and have easy access to the controls 226. In other embodiments, the body may have different designs and the controls 226 may be located in different positions (including on remote devices that communicate with the surgical tool 114 via a communications channel 120) and/or located in multiple positions.

Figure 2D:
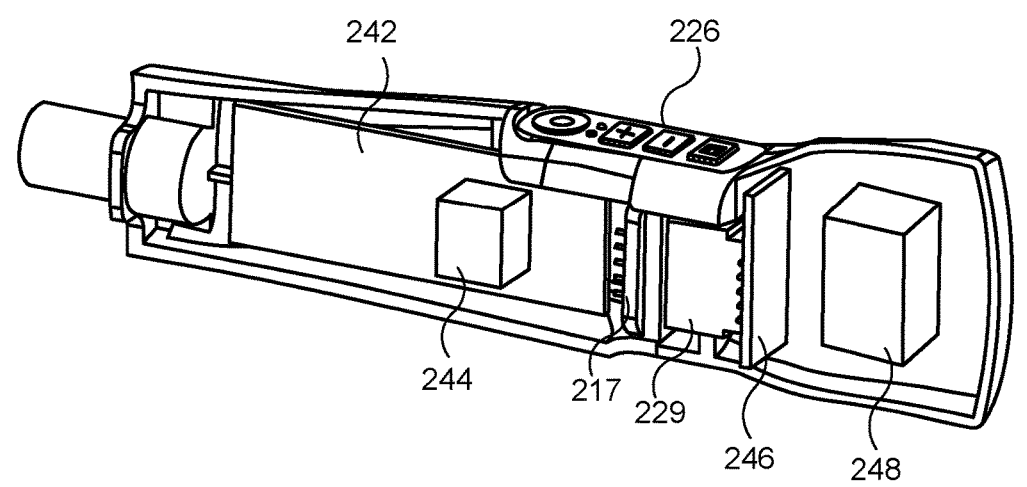
FIG. 2D is a sectional view of the sensor unit and the power unit of the tool when connected with each other, according to one embodiment.

FIG. 2D is a sectional view of the body of one embodiment of the surgical tool 114. Showing the interior of the housings of the sensor unit 210 and the power unit 220. Inside the sensor unit 210 there is a printed circuit board assembly (PCBA) 242 that includes an inertial measurement unit (IMU) 244. The IMU 244 includes one or more sensors 244, such as a gyroscope, an accelerometer, a gravity sensor, a magnetometer, a pressure sensor, a temperature sensor, or the like. Alternatively, some or all of the sensors may be separate components. Regardless, the PCBA 242 causes data generated by the IMU 244 to be sent to the computer 130, either directly via the communication channel 120 or by sending the data to the power unit 220 via the electrical connectors 217 and 229. In some embodiments, the data includes only orientation data for the surgical tool 114.

Inside the power unit is a second PCBA 246 and a battery 248. The second PCBA 246 receives signals from the controls 226 indicating input provided by the surgeon 116. The second PCBA 246 causes data representing the input provided by the surgeon 116 to be sent to the computer (either directly via the communication channel 120 or by sending the data to the sensor unit 110 via the electrical connector 229. The second PCBA 246 may also receive data from the computer 130 indicating information to present to the surgeon 116 (e.g., by lighting up an LED in the controls 226). The battery 248 provides electrical power to the second PCBA 246 and controls 226 as well as to the sensor unit 210 (via the electrical connector 229). The PCBAs 242 and 246 and associated electrical components may be referred to as a controller because they manage the transfer of data to the computer 130 and process any signals received from the computer (in embodiments where the computer may send signals to the tool 114).

During operation, a probe is connected to the mount 218 on the sensor unit 210. The probe includes contact portions that the surgeon 116 places in contact with the surface in which the implant is to be inserted. The surgeon 116 may be directed to contact the surface at specified locations that were selected as part of the surgical planning process. Generally, any configuration of contact portions that define three or more points (or, equivalently, two or more lines or a plane) is sufficient to know the location and orientation of the surgical tool 114 relative to the surface if the contact points are correctly placed at the specified locations. Knowing the relative location of the surgical tool 114, the computer can register the surgical tool 114 by mapping the surgical tool's coordinate system to the coordinate system of the 3D model in the surgical plan. The contact points may be marked (e.g., using a Bovie) to make re-finding the points used for registration easier (e.g., to confirm registration was successful or re-register the probe). Various embodiments of the registration process are described in greater detail below, with reference to FIG. 4.

In some embodiments, once registration is complete, the surgeon 116 may use the surgical tool 114 to align the tip of an implant (e.g., a K-wire) with the desired entry point on the surface in which it is to be inserted (e.g., the scapula) and/or to align the implant with the desired trajectory. The computer 130 may provide a user interface that directs the surgeon 116 to move the surgical tool to position the tip of the implant at the desired entry point. The tip of the implant may then be maintained at the desired entry point or the entry point may be marked (e.g., by touching the implant with a Bovie). The user interface may also direct the surgeon to align the implant along the desired trajectory. Various embodiments of the user interface are described in greater detail below, with reference to FIGS. 5A-H.

Figure 3:
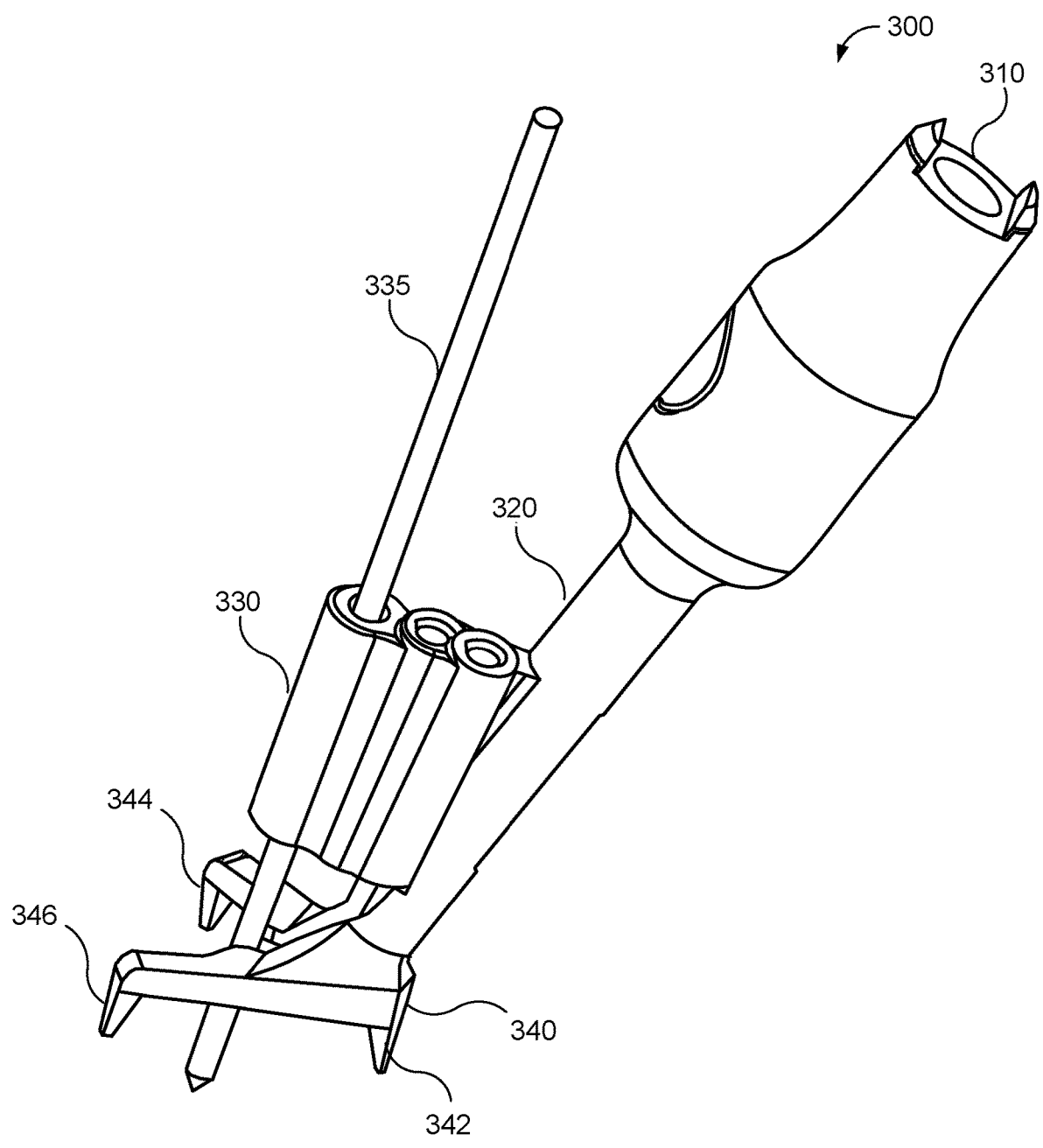
FIG. 3 is a perspective view of a three-point finder probe for insertion of a surgical wire or pin, according to one embodiment.

FIG. 3 illustrates one embodiment of a probe referred to as a three-point finder 300. In the embodiment shown, the three-point finder 300 includes a shaft 320. A mechanical connector 310 for connecting the probe to the mount 218 of the sensor unit 210 is located at a proximal end of the shaft 320. The three-point finder 300 has a head 340 at a distal end of the shaft 320. The head 340 includes a vertex prong 342, a first distal prong (or spike) 344, and a second distal prong (or spike) 346. The surgeon 116 places the tip of each prong 344 and 346 in contact with the surface in which the implant will be inserted during operation at the specified positions. Thus, the tip of each prong is an example of a contact area that may be used during registration of the probe. The three-point finder 300 may also include one or more channels 330 through which the implant 335 (e.g., a K-wire) may pass such that the implant has a known position and trajectory relative to the body of the surgical tool 114. Alternatively, a separate implant guide tool may be used in conjunction with the three-point finder 300.

Other embodiments of the probe have different configurations of contact points. For example, an edge-finder probe includes an adjustable T-shaped jig, with a first adjustable portion of the jig designed to grip the rim around the narrow area of the glenoid above the circular region of the inferior plane (in the anterior-posterior direction), and a second adjustable portion of the jig designed to grip the inferior rim of the glenoid (in the superior-inferior direction). Two patient-specific measurements can be calculated that identify the position where the edge-finder probe will lock into place and restrict movement within a few degrees as long as the surgeon 116 is pushing the edge-finder probe firmly against the glenoid surface. The three points where the edge finder contacts the glenoid surface (anterior, posterior, and inferior) can be used for glenoid registration, since the edge-finder probe attaches to the body of the surgical tool 114 in a fixed, known, orientation.

As another example, an axis-finder probe includes a pair of prongs. The prongs may be separated by a fixed distance or the distance between them may be adjustable (e.g., as directed by the user interface on the computer 130). During registration, the surgeon 116 may be directed to initially place the pair of prongs at specified locations and then rotate the probe around one of the prongs to place the other prong at one or more other specified locations on the arc that the other prong follows when the tool is rotated. Thus, three (or more) contact points and the corresponding position of the surgical tool 114 may be determined for registration.

As a further example, the head of a plane-finder probe may include a portion with a planar surface that is designed to be pressed against the target surface in which the implant is to be inserted. In one embodiment, the surgeon 116 is directed to press the planar surface of the probe against the glenoid surface and find a location and orientation at which the planar surface rests naturally against the glenoid. The tool software calculates three (or more) contact points at which the planar surface is expected to contact the target surface using the 3D model of the glenoid. This may be repeated for two (or more) different orientations of the plane-finder tool. The resulting contact points may be used for registration and may have the advantage that the surgeon 116 does not need to manually identify specific contact points but rather presses the tool 114 against the glenoid and finds a natural resting position.

In some embodiments, the planar surface of the plane-finder includes a flat edge and the surgeon 116 may be directed by the user interface to align the flat edge with an easily identifiable line on the glenoid surface by placing the flat edge passing through two (or more) specified points. The points on the flat edge that pass through the two specified points define two contact areas that can be used for registration. In one embodiment, the planar surface is a circular segment and one or more points along the curved edge of the circular segment that are in contact with surface (e.g., at the mid-point of the curved edge) may also be used for registration (in addition to the points along the flat edge). In other embodiments, some or all of the contact points determined are in an interior portion of the planar surface (i.e., not along one of the edges) and the edges of the surface may be used by the surgeon 116 to visually confirm that the alignment of the surgical tool 114 is correct during or after registration.

One of skill in the art will recognize that other arrangements of contact areas on probe heads may be used to define a set of points, lines, and/or planes for registration. Because the contact areas of the probe head have a known spatial relationship to the body of the surgical tool 114, if the surgeon 116 aligns these contact areas with specified locations on the surface, the coordinate space of the 3D model used for surgical planning may be mapped to the surface and the coordinate system of the position data generated by the surgical tool. Thus, assuming registration was successful, as the surgeon 116 moves the surgical tool 114, its current orientation can be accurately depicted in the user interface with a virtual representation of the tool and the 3D model.

Example Software and User Interfaces

Figure 4:
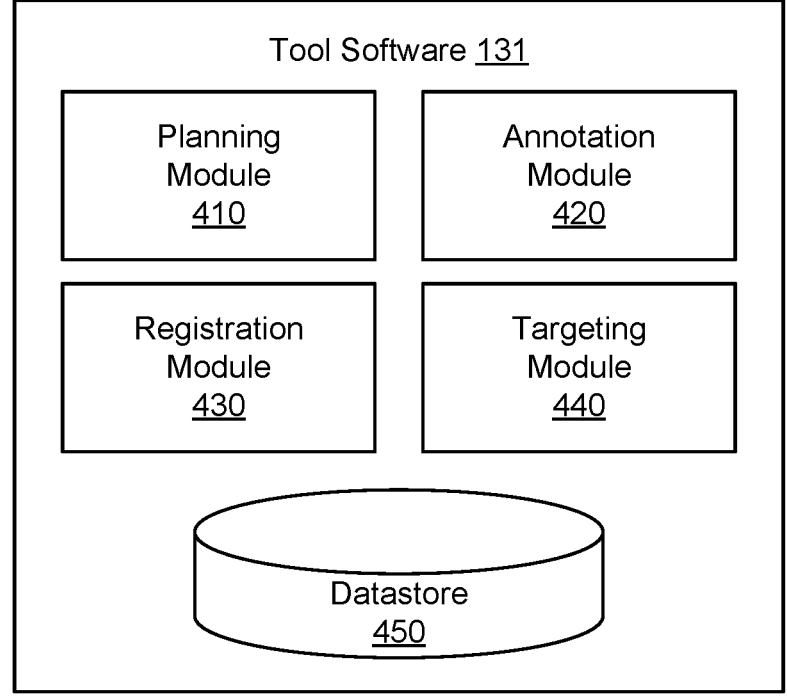
FIG. 4 is a block diagram of the tool software of the computer shown in FIG. 1, according to one embodiment.

FIG. 4 illustrates one embodiment of the tool software 131 that may be used to provide navigation-guidance for operation of the surgical tool 114. In the embodiment shown, the tool software 131 includes a planning module 410, an annotation module 420, a registration module 430, a targeting module 440, and a data store 450. In other embodiments, the tool software 131 may include different or additional components. Furthermore, the functionality may be distributed among the components in different manners than described.

The planning module 410 provides a user interface for the surgeon 116 to make a surgical plan in advance of the surgery. In one embodiment, the planning module 410 receives a 3D model of the shoulder to be operated on. The 3D model may be generated from CT-imaging scans or data generated using other suitable imaging techniques. The planning module 410 enables the surgeon 116 to view the 3D model and select an entry point and trajectory for the implant, which are saved as part of the surgical plan. For example, the surgeon 116 may tap or click on a desired entry point and drag or otherwise align a virtual representation of the implant to change the trajectory at which it enters the surface at the desired entry point. The surgical plan may be made on the computer 130 that will be used during the surgery or saved to a non-transitory computer-readable memory for later access by the computer 130, such as a network-accessible drive or a USB drive that the surgeon 116 connects to the computer 130 when preparing for surgery.

The annotation module 420 provides a user interface for the surgeon 116 to select points on the 3D model that will be used for registration. In one embodiment, the surgeon 116 selects a set of points (e.g., three points if a three-point finder probe will be used) that they believe will be easy to identify and probe on the real bone surface. The surgeon 116 may select the points using any suitable method, such as clicking or tapping on desired points on the 3D model. The selected points may be stored as an annotation to the 3D model in the surgical plan prior to beginning the surgery.

Additionally or alternatively, the points may be identified while the surgery is underway. Identifying the points during the surgery may be useful for complex surgeries where the anatomy is modified by the surgery prior to insertion of the implant. Identifying the points during the surgery may also be useful where the surgeon 116 determined once surgery is underway that the 3D model included in the surgical plan was inaccurate or where the initially selected registration points cannot be identified on the actual bone surface. For example, the surgeon 116 may find out after exposure that the glenoid has osteophytes or wear on one edge that is different from the 3D model. The surgeon 116 may then decide to re-annotate using a different portion of the 3D model of the glenoid by selecting points on different areas.

Figure 5A:
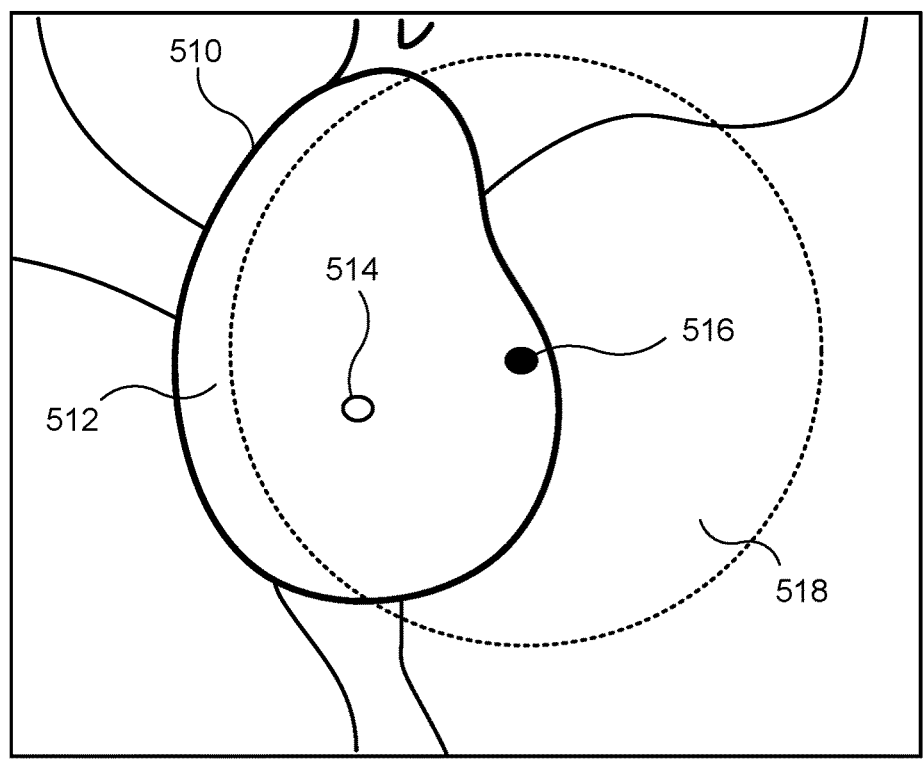
FIGS. 5A and 5B illustrate an example user interface for selection of a vertex point and a pair of distal points for a three-point finder probe, according to one embodiment.
Figure 5B:
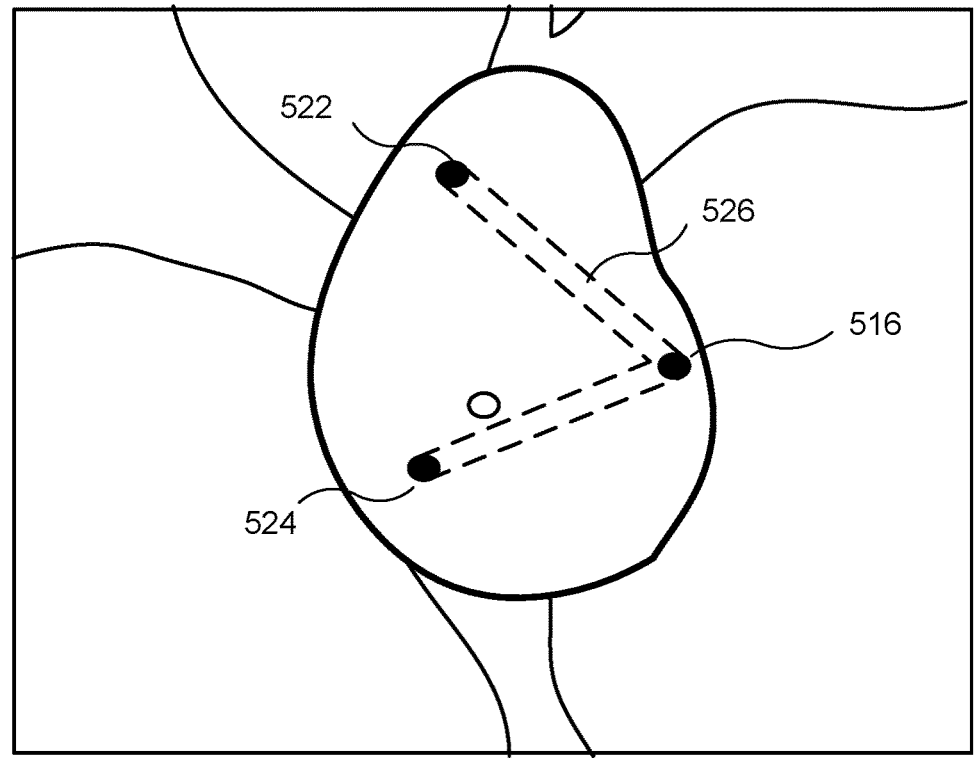

FIGS. 5A and 5B illustrate an example user interface for selecting registration points for a three-point finder probe. In FIG. 5A, a view of a 3D model of a patient's scapula 510 is displayed. The 3D view incudes a depiction of the glenoid surface 512. The desired entry location 514 selected by the surgeon 116 (e.g., by clicking or tapping on the desired location) can be seen and the surgeon has selected an identifiable vertex point 516 at which one of the prongs of a three-point finder probe should contact the glenoid. The user interface shows a view of a sphere 518 indicating the possible positions of distal points for the three-point finder probe if the vertex point is correctly positioned at the selected location 516. In FIG. 5B, the surgeon 116 has selected a pair of distal points 522 and 524.

In one embodiment, the distal points 522 and 524 are selected by rotating a visualization of the head of the probe 526 around the vertex point 516. Because the relative positions of the prongs of the probe are known, selecting an orientation of the probe identifies the pair of distal points 522 and 524. Alternatively, the surgeon 116 may tap or click on a position for one of the distal points (e.g., point 522) and the other may be automatically placed. Note that for some configurations of probe, the surgeon 116 may select a single point and the others may be automatically placed by the software. Regardless of how they are placed, the three points define a triangle on the surface of the glenoid 512 which may be used for registration of the three-point finder probe.

Figure 5C:
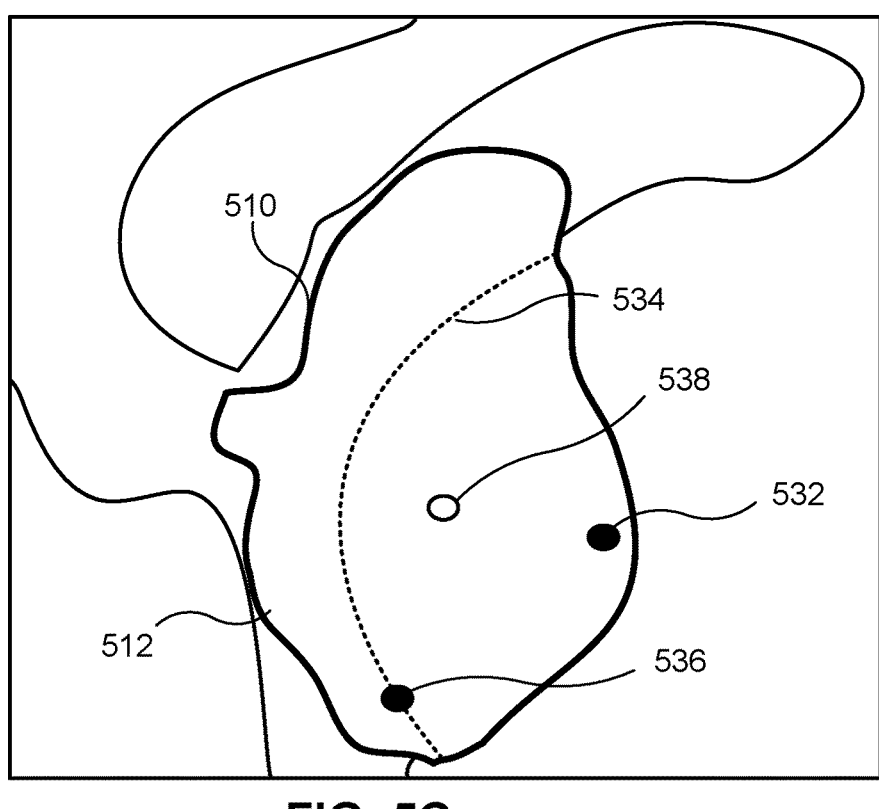
FIGS. 5C and 5D illustrate an example user interface for selection of a vertex point and a pair of distal points for an axis finder probe, according to one embodiment.
Figure 5D:
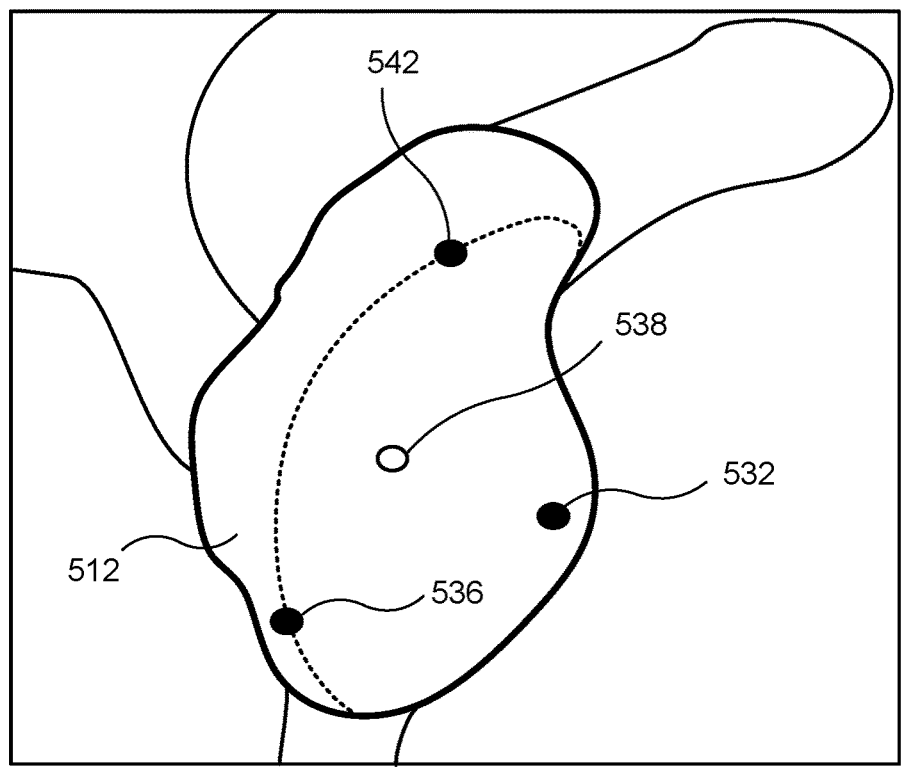

FIGS. 5C and 5D show a second example of a user interface for selecting registration points. The second example may be used with an axis finder probe. In FIG. 5C, as with the first example user interface, a view of the 3D model 510 including the glenoid surface 512 is displayed. The desired entry location 538 for the implant is also visible. The surgeon 116 has selected a first contact point 532 for a first prong of the axis finder probe. The user interface includes an arc 534 indicating all of the possible locations at which a second prong of the axis finder may contact the glenoid surface 512. The surgeon 116 has selected a second contact point 536 on the arc 534 for a second prong of the axis finder tool. In FIG. 5D, the surgeon 116 has selected a third contact point 542 on the arc 534 for the second prong of the axis finder tool. Thus, the surgeon 116 has selected an appropriate set of three points on the glenoid surface 512 for registering the axis finder probe.

Referring again to FIG. 4, the registration module 430 provides a user interface that guides the surgeon 116 through the registration process for the surgery. The registration module 430 causes the display of a view of the 3D model with one or more points or lines with which the surgeon 116 aligns corresponding portions of the surgical tool 114. In one embodiment, using a three-point finder probe, the surgeon 116 is shown a view similar to that shown in FIG. 5B that identifies the three points that should be contacted by the prongs of the probe. The surgeon places the prongs of the probe at the corresponding locations on the physical surface and indicates when the surgical tool 114 is correctly positioned (e.g., by pressing a button of the controls 226 of the surgical tool). In other embodiments, different user interfaces may be used. For example, for registering an axis finder probe, the user interface may prompt the surgeon 116 to first position the prongs of the probe to contact two identified points on the surface and then rotate the probe around one of the prongs until the other prong contacts the surface at a third identified point on the surface.

If the surgeon 116 activates a physical control (e.g., pressing a button) to indicate when the surgical tool 114 is correctly positioned/aligned for registration, the activation of the control may vibrate or otherwise move the surgical tool 114. Various techniques maybe used to compensate for any such movement and mitigate the risk of the surgical tool being incorrectly registered. In one embodiment, the software provides a three second countdown after the surgeon 116 presses a physical button to give a chance to the surgeon to hold the instrument as still as possible before the orientation is measured by the sensors. In another embodiment, the registration may instead be triggered by a gesture (e.g., moving the surgical tool 114 in a certain way) to avoid the potentially harsh vibration caused by pressing a physical button. In a further embodiment, the registration process may be triggered once the sensor data indicates that the surgeon 116 has held the instrument still (e.g., the orientation has changed by less than a threshold amount around each axis or collectively) for a predetermined amount of time (e.g., three seconds). In other embodiments, other signals may be used to trigger registration, such as a verbal command that is picked up by a microphone and processed by the computer 130, a gesture performed with a body part not in direct contact the surgical tool and picked up by a camera, an input provided directly to the computer (e.g., by tapping a button on a touchscreen), and the like.

Once the surgeon 116 indicates that initial registration has been completed, the user interface may prompt the surgeon to verify that the registration is sufficiently accurate. For example, the user interface may direct the surgeon 116 to rotate the probe around one of the prongs such that the other prongs contact the surface at additional identified contact points. If the registration is accurate, the position of the probe on the physical surface will agree with the position data reported by the IMU 244, and thus the position of a virtual representation of the probe in the user interface should match the position of the physical probe. The surgeon 116 may perform additional manual checks by moving the probe and confirming that the movement of the virtual representation of the probe in the user interface matches the movement of the physical probe.

In various embodiments, the registration may be tested with direct feedback, indirect feedback, or both. Direct feedback checks may be performed just after having completed the registration. One prong (e.g., the prong contacting the vertex point) is kept in contact with the surface and the surgical tool 114 is rotated about it. The surgeon 116 confirms that the virtual instrument displayed in the user interface moves in sync with the actual instrument.

The synchronization between the actual and virtual instrument can be confirmed by observing both instruments crossing the edges or other identifiable features of the surface at the same spot/time (x-axis and y-axis), hovering over the same landmark at the same spot/time (x-axis and y-axis), and/or by confirming contact with the surface (z-axis). The surgeon 116 can look at any of the free prongs (except the one on the pivotal point) to align with features on the surface and confirm the registration. The free prongs do not necessarily need to reach the specific feature used for confirming the registration but can pass in proximity and build confidence over the registration by means of multiple features tested. The registration module 420 can also provide feedback when two virtual models are interfering, e.g., by changing colors or by showing a popup window. The surgeon 116 can use this information to pivot the instrument and land the free prongs on different points of the surface to confirm that the virtual model is actually touching the surface at the same time.

If the surgeon 116 is not satisfied with the registration, they may restart the process (e.g., by pressing a button of the controls 226 of the surgical tool, pressing a button in the user interface, or issuing a verbal confirmation that is picked up by a microphone and processed by the computer 130, etc.). Conversely, if the surgeon 116 is satisfied with the registration, they may provide user input indicating registration was successfully completed.

As example approach using indirect feedback may be referred to as two-step registration. Two-step registration includes selection of more points than is mathematically necessary to perform the registration. For example, with a three-point finder, the surgeon 116 may be directed to choose multiple sets of points to register, while keeping the vertex point (or another rotation point) fixed. If the annotation allows the selection of multiple positions, the software can calculate the rotation to get from a first position to one or more additional positions. Once the surgeon 116 confirms the additional position (or positions, depending on the choice made during annotation), the software checks if the actual rotation between the first position and the additional position or positions is the same (or within a tolerance error) as the one calculated on the virtual model. This is not a direct validation of the registration but confirms that the surgeon 116 has recognized two (or more) sets of features on the glenoid within a certain angular error from each other. In theory the surgeon could find the same angular relation between completely different sets of features, but with the glenoid being an irregular shape, this is unlikely to happen.

The targeting module 440 provides a user interface for display to guide the surgeon 116 to locate the desired entry point and/or entry trajectory for the implant. In some embodiments, the targeting module 440 first directs the surgeon 116 to align the surgical tool 114 to place the tip of the implant at the desired entry point and then directs the surgeon to change the orientation of the surgical tool (and hence the implant) to have the desired entry trajectory. In other embodiments, the targeting module 440 directs the surgeon to use the surgical tool to identify and mark the desired entry point (e.g., using a laser aligned with the axis of surgical tool or using a Bovie, etc.) and a separate tool may be used to insert the implant.

In one embodiment, using a three-point finder probe, position data generated by the surgical tool 114 is orientation data and the targeting module 440 identifies the desired entry point based on the principle that a line will intersect with a plane at different locations depending on the orientation of that line. The line can be the axis of a channel 330 of the surgical tool 114. The channel 330 can be mounted with its axis at an angle on the surgical tool 114. Alternatively, the line can be defined by another type of line indicator, such as a laser or other point indicator with known alignment relative to the surgical tool 114. As the surgical tool 114 is rotated about its pivot point (e.g., the prong in contact with the vertex point), the channel 330 (or other line indicator) will aim at different points on the surface below, allowing the targeting of a wide set of coordinates.

Figure 5E:
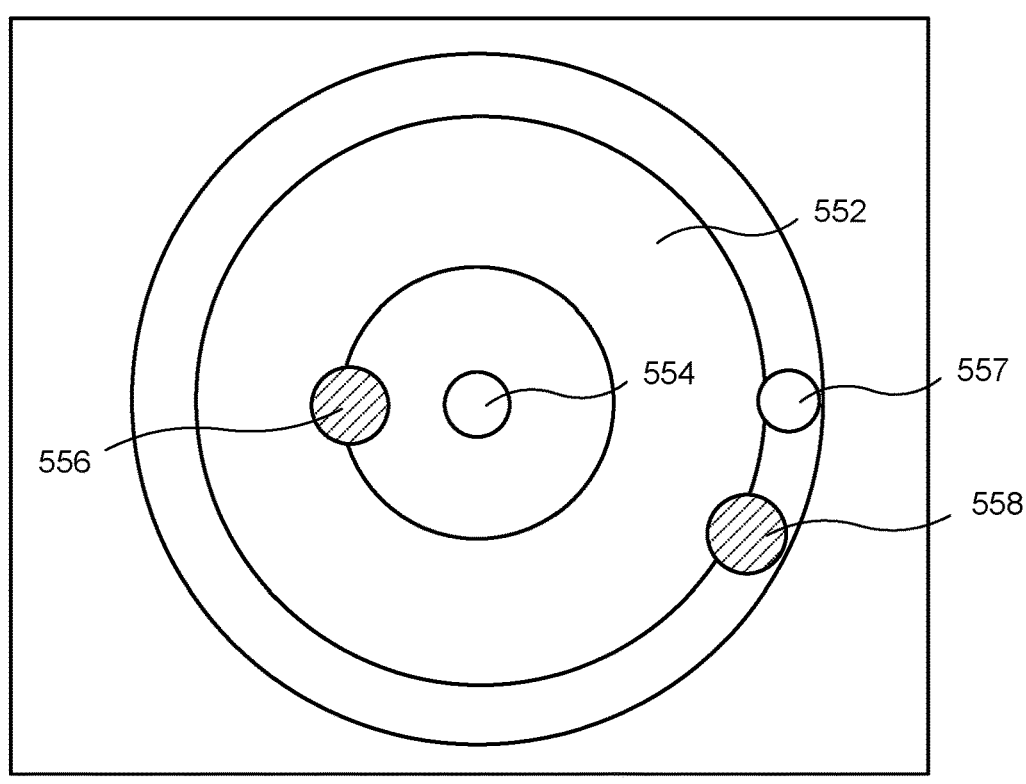
FIGS. 5E and 5F illustrate an example user interface for targeting a planned entry point for an implant, according to one embodiment.
Figure 5F:
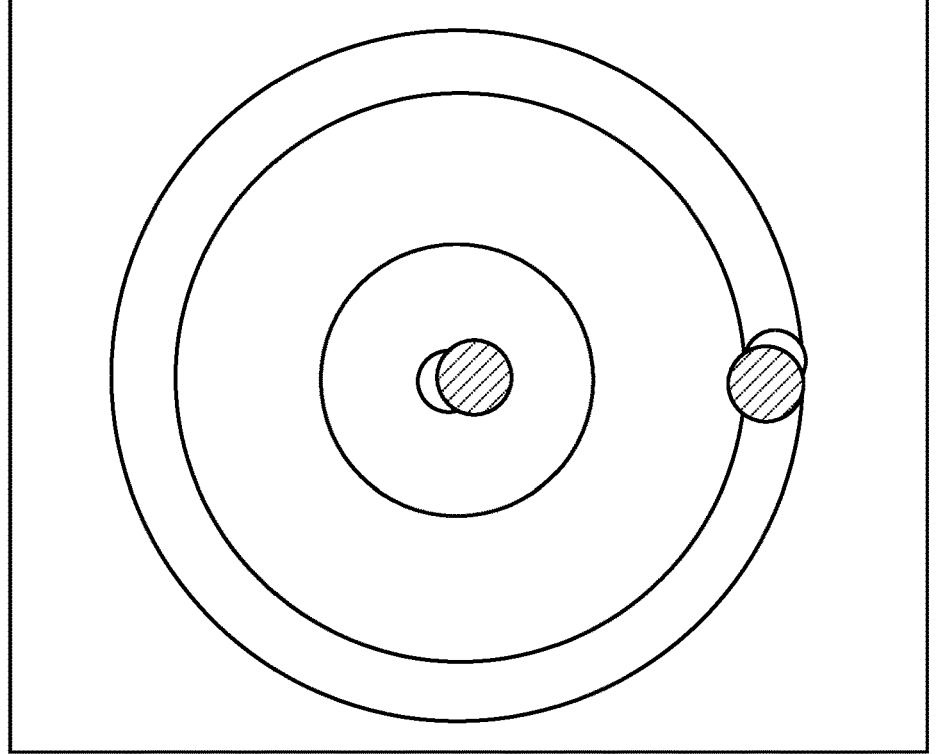

The user interface to target the desired entry point can take several forms showing the virtual model of the instrument or a cross-hair targeting interface. The desired entry point may be targeted by any rotation of the surgical tool 114 around the vector between the pivot point (e.g., the vertex point) and the desired entry point. FIGS. 5E and 5F illustrate an example user interface for aligning the axis of a channel 330 (or other line indicator) with the desired entry point on the surface. In the embodiment shown, the user interface guides the user to move the instrument to the entry-point targeting orientation that is closest to the current orientation.

Specifically, the user interface includes a set of concentric circles 552 around a central target point 554 that corresponds to the tool having the desired pitch and yaw. An alignment indicator 556 indicates where the axis of the channel 330 is currently pointing, guiding the surgeon 116 to tilt the surgical tool 114 around the pivot point until the alignment indicator 556 aligns with the central target point 554. The user interface also includes a rotation target 557 and a roll indicator 558 that guides the surgeon to rotate the surgical tool 114 around the pivot point until the rotation target 557 and the roll indicator 558 align.

As shown in FIG. 5F, when the alignment indicator 556 and the roll indicator 558 are sufficiently aligned (within a pre-specified tolerance) with the central target point 554 and rotation target point 557, respectively, the user interface can provide a visual indication that the correct orientation of the surgical tool 114 has been achieved. The visual indication can be the appearance of a logo or symbol, a change in color of a background, a change in color or size of the concentric circles, and/or any other visual indication that the surgical tool 114 is correctly positioned. Additionally or alternatively, an audio or tactile indication of correct positioning of the surgical tool 114 may be provided. Furthermore, an indication (e.g., illumination of an indicator light) may be provided on the surgical tool 114.

Once the desired entry point is found, the surgeon 116 can provide confirmation (e.g., by pressing a button of the controls 226) and the targeting module 440 may transition to finding the desired insertion trajectory for the implant. The same surgical tool 114 can be used or a separate tool configured specifically for aligning the implant with the desired trajectory may be used. Using a combined tool has the advantage that a single tool may be used for targeting and insertion of the implant (e.g., the alignment and insertion of a K-wire) while using separate tools may allow each one to be better configured for the corresponding task (e.g., by being smaller, reducing the risk of causing unnecessary damage to soft tissue).

In one embodiment, once the surgical tool 114 is oriented so that the selected channel 330 is aiming at the desired entry point, a K-wire is pushed through the channel until contacting the bone at the desired entry point. The surgeon 116 holds the K-wire in contact with the bone and pivots the instrument around the contact point between the K-wire and the bone. The registration prongs may be lifted from the bone at this point, allowing the targeting of the K-wire trajectory. Alternatively, in embodiments where separate tools are used, the surgeon 116 may use an insertion/orientation tool to place the tip of the K-wire at the desired entry point marked by the registration tool and pivot the insertion/orientation tool around the contact point between the tip and surface to identify the desired trajectory.

Figure 5G:
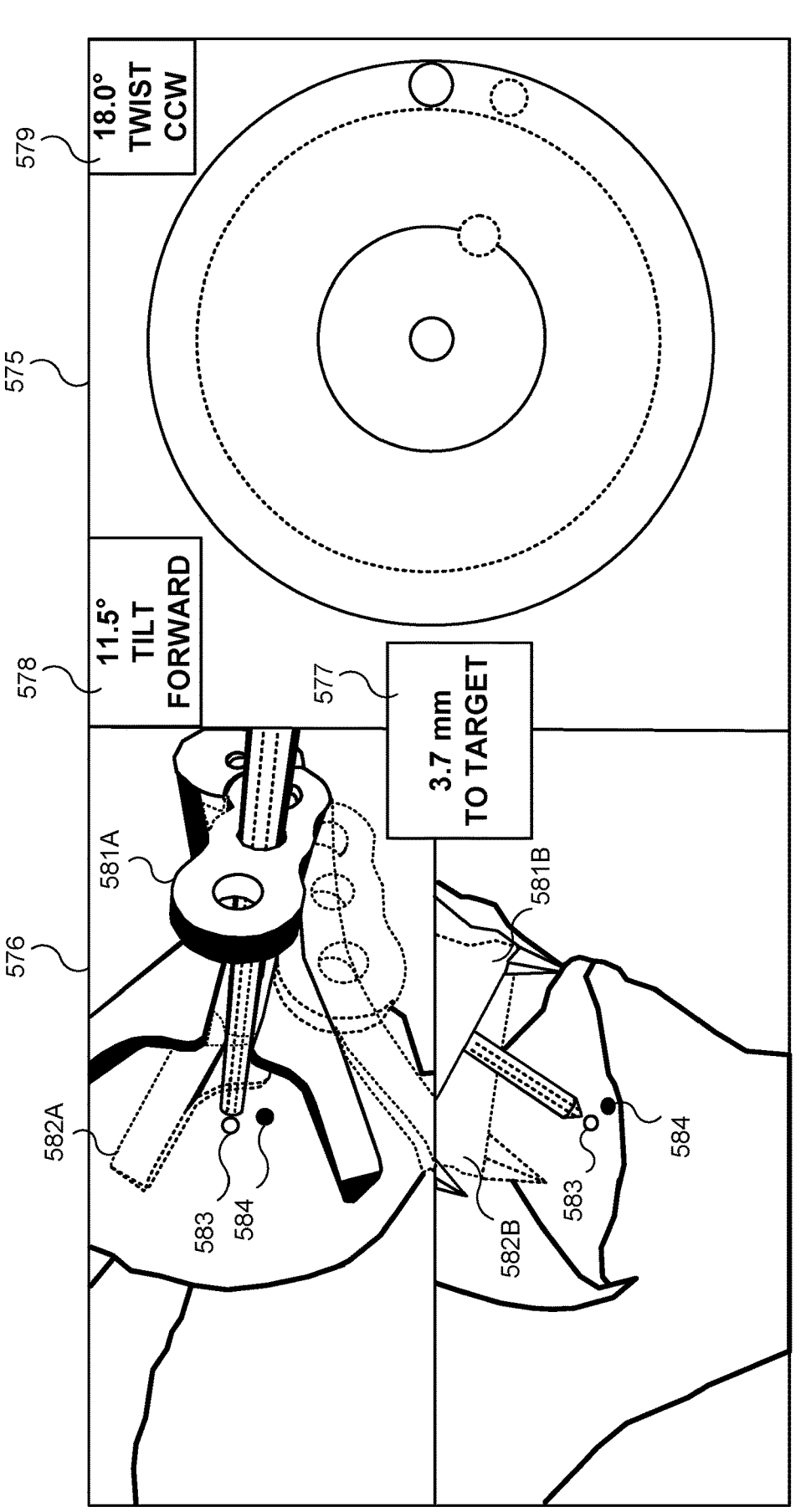
FIGS. 5G and 5H illustrate another example user interface for targeting a planned entry point for an implant, according to one embodiment.
Figure 5H:
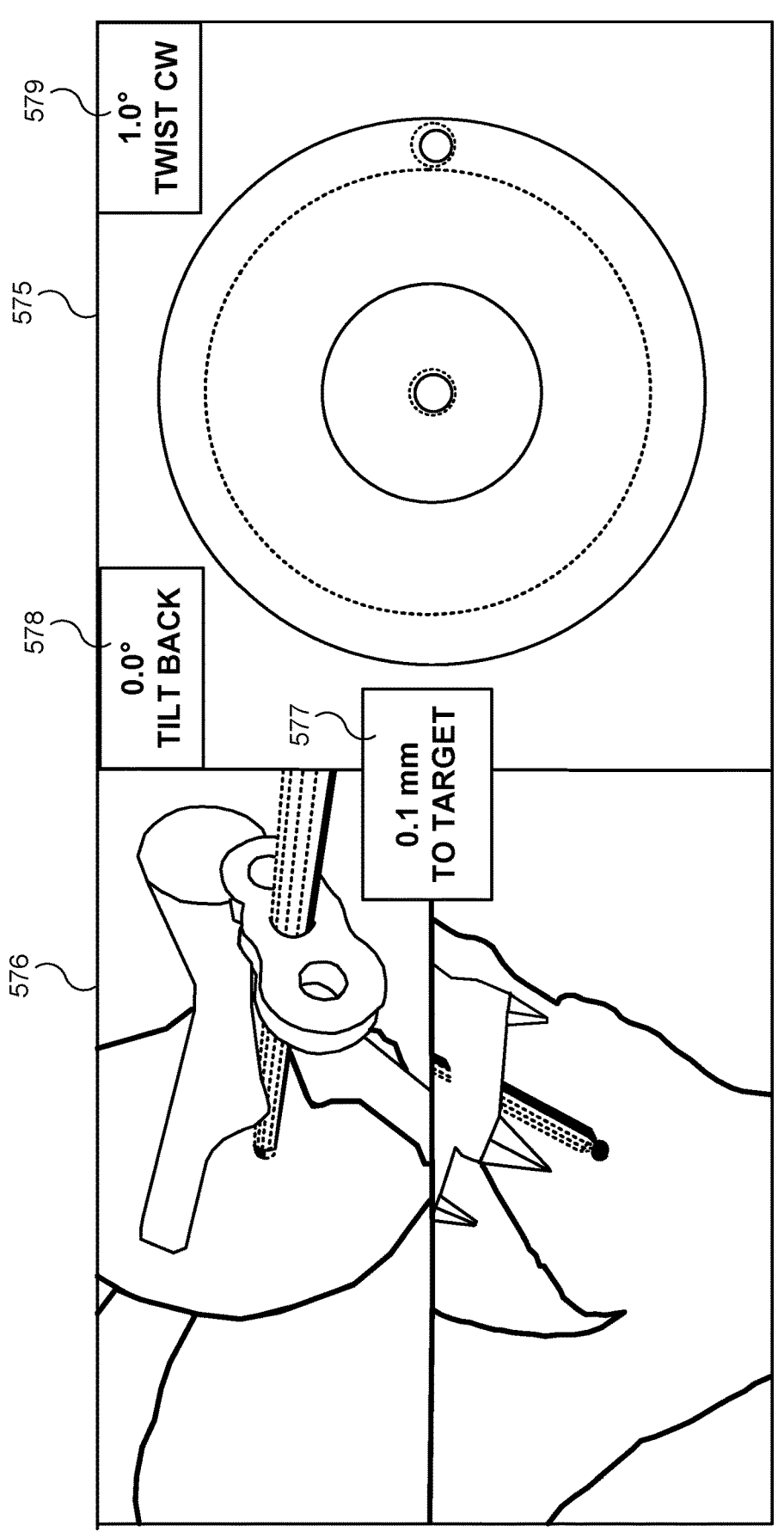

FIGS. 5G and 5H illustrate a second example user interface for aligning the axis of a channel 330 (or other line indicator) with the desired entry point on the surface. In the embodiment shown, as well as a two-dimensional targeting portion 575 that is similar to FIGS. 5E and 5F. The user interface also includes a three-dimensional targeting portion 576 that shows one or more three-dimensional representations of the surgical tool 114. In the embodiment shown, the three-dimensional targeting portion 576 shows two 3D models. One represents how the surgical tool 114 is currently aligned and one represents the entry-point-targeting orientation that is closest to the current tool orientation. Each model shows a visual representation of the current orientation of the tool 581A and 581B and a visual representation of a current target orientation of the tool 582A and 582B. Both models update based on the sensor data received from the surgical tool 114. The 3D models also include visual indications of a point at which the implant is currently pointed 583 and the target entry point 584. Because any rotation of the surgical tool 114 around the axis between the desired entry point and the pivot point of the tool is valid solution, there are effectively infinite valid alignments for the surgical tool. Consequently, the software 131 may suggest the closest one to the current position of the instrument.

In some embodiments, the target orientation for the tool 114 changes dynamically to guide the user to the orientation that targets the entry point that is closest to the current orientation of the tool.

As the surgeon 116 moves the surgical tool 114, the three-dimensional representation(s) are updated to show the position of the surgical tool relative to the target orientation and target entry point, as estimated from the sensor data generated by the tool. The user interface also includes one or more numerical indicators, such as a distance indicator 577, a tilt indicator 578, and a twist indicator 579. The distance indicator 577 indicates the distance from the point on the surface at which the tip of the implant is currently pointed to the target entry point. The tilt indicator 578 and the twist indicator 579 indicate the angle by which the tool 114 should be tilted and twisted, respectively, to point the channel of the tool at the desired entry point. In FIG. 5G the tool is not yet aligned and in FIG. 5H the tool is aligned. One or more further visual indications of the alignment may be provided, such as the display of an icon or logo, change in background color, or the like. The combination of the two-dimensional and three-dimensional visualizations may help the surgeon 116 understand how the orientation of the tool needs to be adjusted to correctly align the tip of the implant with the desired entry point.

Figure 5I:
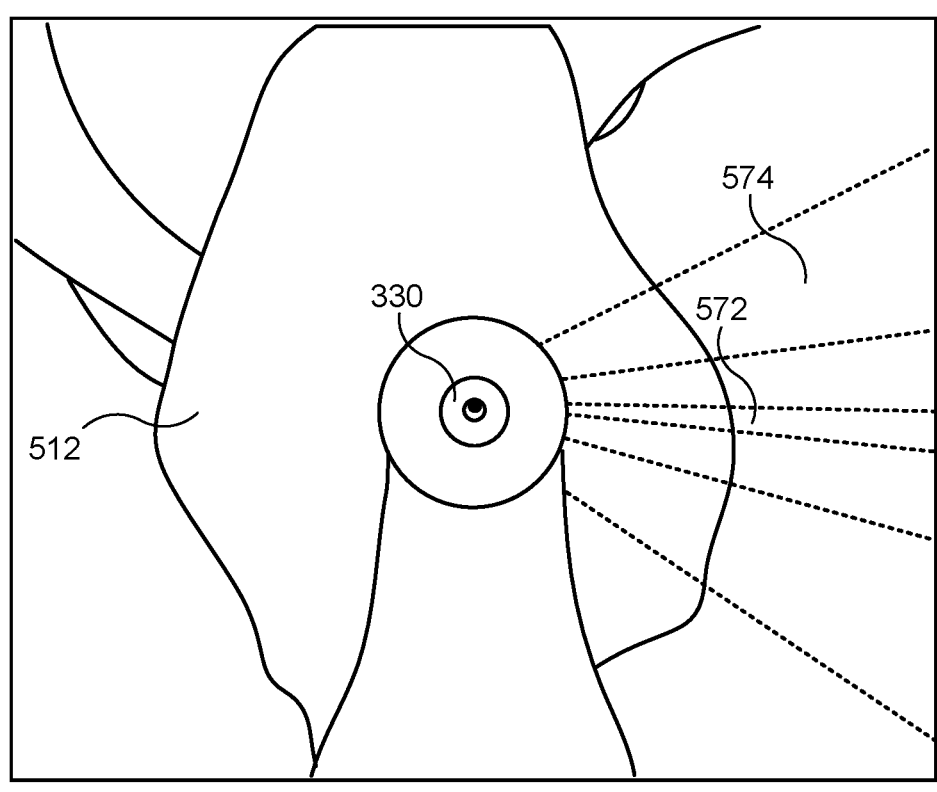
FIGS. 5I and 5J illustrate an example user interface for aligning the surgical tool to insert the implant along a planned trajectory, according to one embodiment.
Figure 5J:
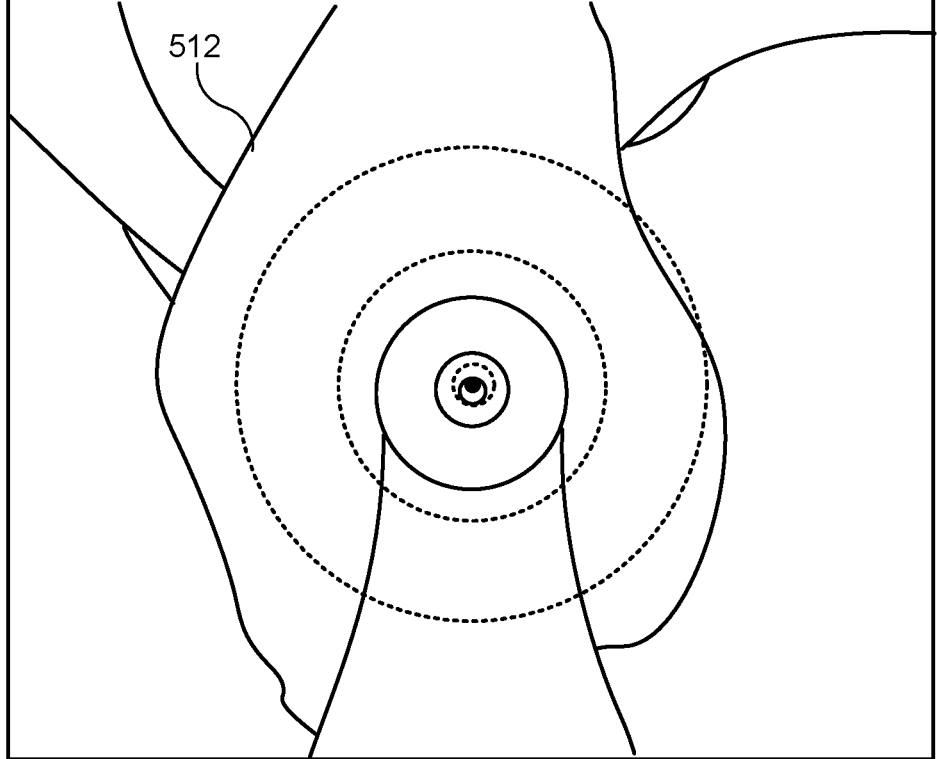

FIGS. 5I and 5J illustrate an example user interface for guiding the surgeon 116 to align the K-wire (or other implant) with the desired trajectory. In the embodiment shown, the user interface includes a top-down view of the glenoid surface 512 and a virtual representation of the channel 330 of the surgical tool 114. In FIG. 5I, an indicator of the desired trajectory 572 can be seen to the right hand side of the image. The indicator of the desired trajectory 572 is surrounded by concentric tubes 574 (e.g., having different shadings) indicating proximity to the desired trajectory 572. As the surgeon 116 pivots the surgical tool 114 to the right, the indicator on the desired trajectory moves closer to the axis of the channel 330. When the surgical tool 114 is aligned correctly to have the K-wire at the desired insertion trajectory, the concentric tubes 574 appear as concentric circles surrounding the axis of the channel 330. One or more additional indicators may be provided that the surgical tool 114 is correctly aligned, including displaying an icon or logo in the user interface, changing a background color of the user interface, changing a size of the concentric tubes 574, lighting an indicator light on the surgical tool, playing an audio indication, providing a tactile indication, and/or the like.

Once the user interface indicates that the K-wire tip has been placed at the desired entry point and the K-wire is oriented with the desired insertion trajectory, the surgeon 116 may visually verify that the positioning of the K-wire looks correct and insert it into the bone. In some embodiments, the surgeon 116 may provide user input (e.g., by pressing a button of the controls 226) to confirm that targeting has been completed and the K-wire is ready to be inserted.

Figure 5K:
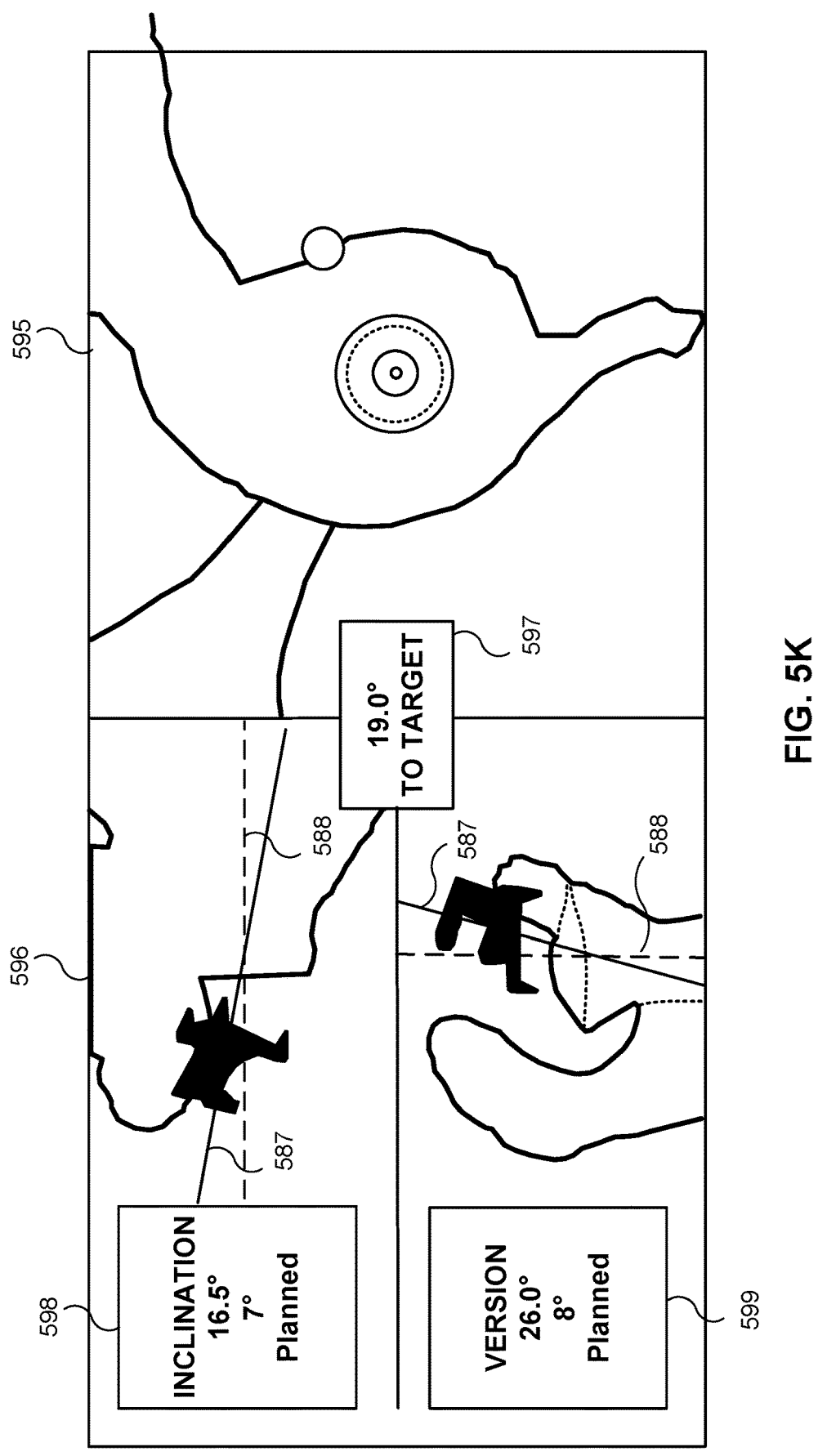
FIGS. 5K and 5L illustrate another example user interface for aligning the surgical tool to insert the implant along a planned trajectory, according to one embodiment.
Figure 5L:
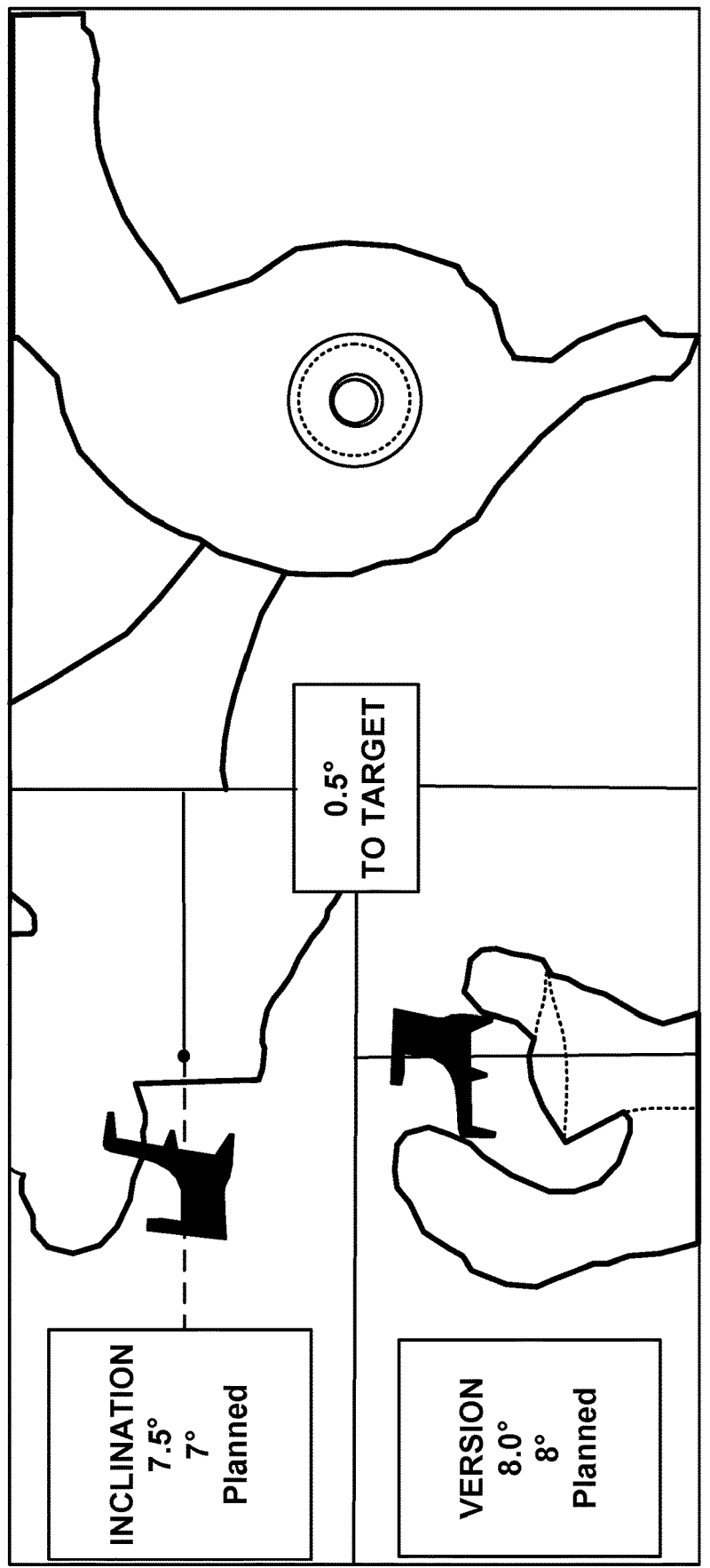

FIGS. 5K and 5L illustrate another example user interface for aligning the surgical tool to insert the implant along a planned trajectory. In the embodiment shown, as well as a two-dimensional trajectory alignment portion 595 that is similar to FIGS. 5I and 5J. The user interface also includes a three-dimensional trajectory alignment portion 596 that shows one or more three-dimensional representations of the surgical tool 114 indicating how the implant is currently aligned relative to the desired trajectory. As the surgeon 116 moves the surgical tool 114, the three-dimensional representation(s) are updated to show the alignment of the implant relative to the desired trajectory as estimated from the sensor data generated by the tool. For example, the user interface can indicate the current trajectory with a first line 587 and the desired trajectory with a second line 588 (which may be visually distinguished from the first line by color, thickness, dashing, and/or the like).

The user interface also includes one or more numerical indicators, such as indicators of the angle to the target alignment 597, the inclination relative to the planned inclination 598, and the version relative the planned version 599. In FIG. 5K the implant is not yet aligned with the desired trajectory and in FIG. 5L the implant is aligned. One or more further visual indications of the alignment may be provided, such as the display of an icon or logo, change in background color, or the like. The combination of the two-dimensional and three-dimensional visualizations may help the surgeon 116 understand how the orientation of the tool needs to be adjusted to correctly align the implant with the desired trajectory. The software may provide one or more additional or alternative forms of feedback regarding alignment, including acoustic and/or haptic feedback.

Referring once again to FIG. 4, the datastore 450 includes one or more computer-readable media configured to store the software and/or data used by the tool software 131. For example, the datastore 450 can include executable code for the modules of the tool software described above. The datastore 450 may also store the surgical plans used during surgery, information gathered during the surgery, diagnostic data for the surgical tool 114, and the like. Although the datastore 450 is shown as a single entity within the tool software 131, in other embodiments, the code and/or data used by the tool software 131 may be split across multiple datastores 450, some or all of which may be accessed via a network.

Example Implant Location Verification Tool

Figure 6A:
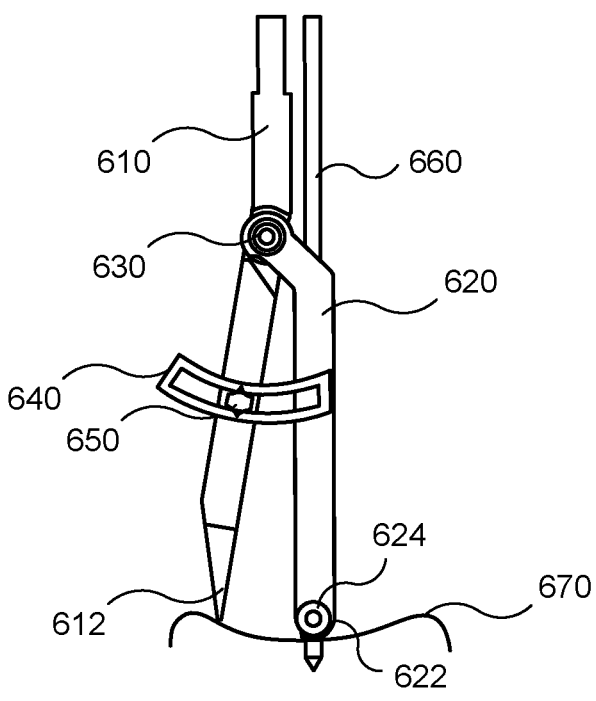
FIGS. 6A and 6B illustrate a tool for confirming an implant was inserted at the planned entry point, according to one embodiment.
Figure 6B:
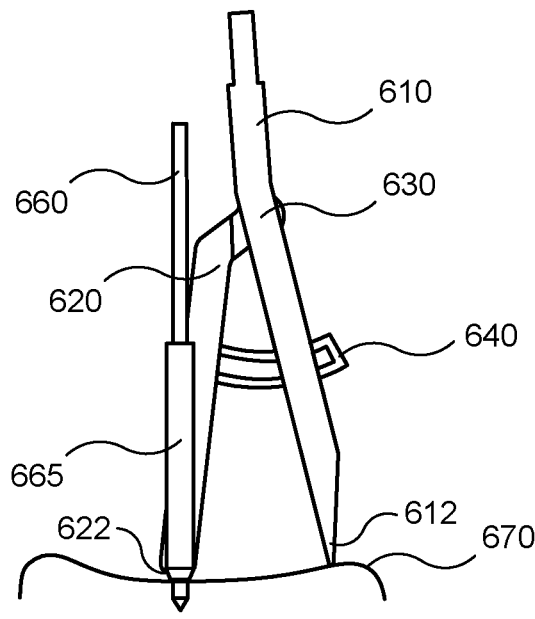

FIGS. 6A and 6B illustrate one embodiment of a tool for confirming an implant was inserted at the planned entry point. In the embodiment shown, the tool includes a first arm 610 and a second arm 620, connected by a central pivot 630. The central pivot 630 connects the proximal end of the second arm 620 to a point on the first arm 610 about one third of the way from its proximal end towards its distal end. The distal end of the first arm 610 ends in a spike 612. The distal end 622 of the second arm 620 may have a flat or rounded end, or may similarly end in a point or spike. The first arm 610 may rotate around the central pivot 630 such that the spikes 612 and 622 move towards or away from each other.

A channel 665 is attached to the second arm using a channel pivot 624. The channel 665 can be slid over an implant 660 (e.g., a K-wire) after the implant has been inserted into a surface 670 (e.g., using the surgical tool 114). Thus, the distal end of the second arm 620 contacts the surface 670 adjacent to the entry point of the implant 660. The first arm 610 may be moved around the central pivot 630 and the tool rotated around the implant 660 to place the tip 612 of the first arm 610 at one of the points used for registration (e.g., the vertex point for a three-point finder probe). The scale 640 and marker 650 can be used to measure the distance between the tip of the first arm 612 and the tip of the channel 665. This process may be repeated for some or all of the registration points. Thus, the accuracy with which the implant 660 was placed on the surface 670 can be verified by comparing the measured distances to the registration points to the expected distances between the registration points and the desired entry point in the 3D model used in the surgical plan. If one or more of the measured distances (or a mean of measured distances) differs from the expected distances by more than a threshold amount, the surgeon 116 may elect to remove the implant and reinsert it into the surface 670.

Example Methods

Figure 8:
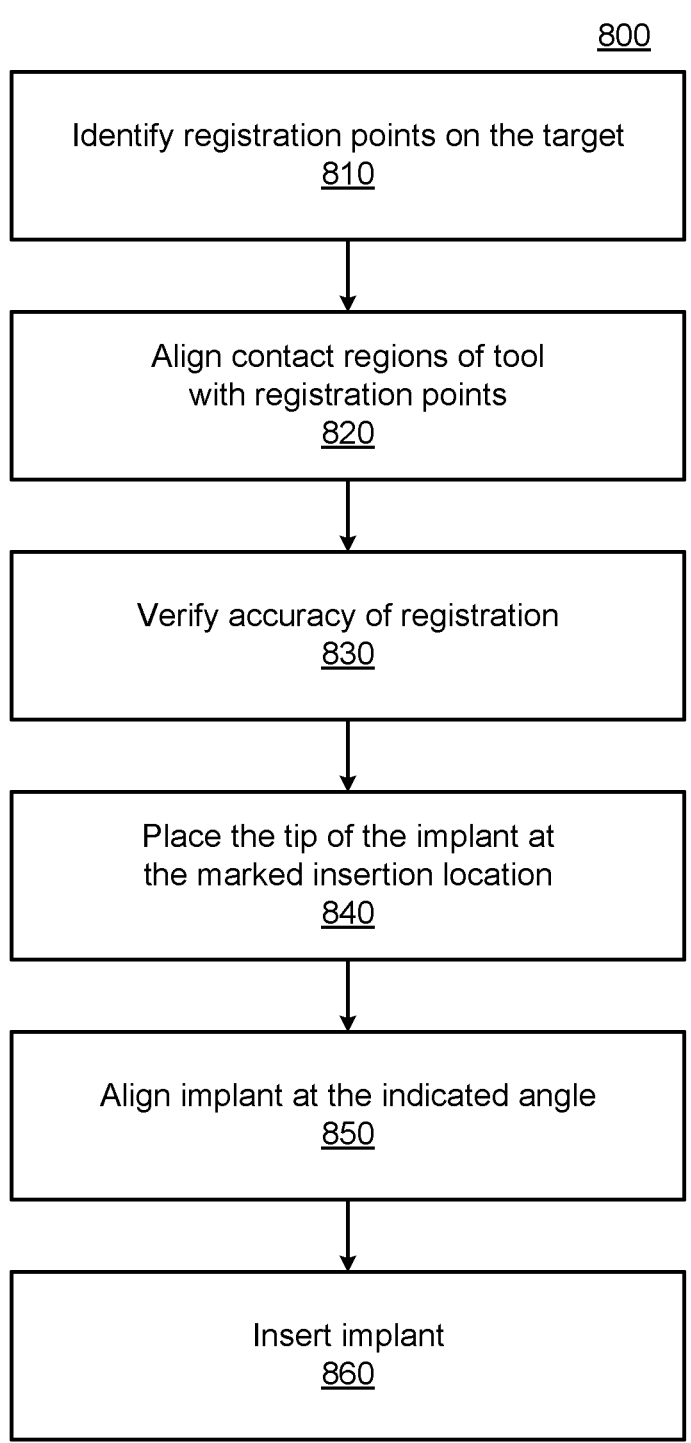
FIG. 8 is a flowchart of an example method for inserting an implant using the tool, according to one embodiment.

FIGS. 7 and 8 illustrate embodiments of methods involving use of a tool (e.g., surgical tool 114) to insert an implant. The steps of FIGS. 7 and 8 are illustrated from the perspective of various entities performing the methods. However, some or all of the steps may be performed by other entities or components. In addition, some embodiments may perform the steps in parallel, perform the steps in different orders, or perform different steps.

FIG. 7 illustrates one embodiment of a computer-implemented method 700 for guiding the insertion of an implant with a tool. In the embodiment shown, the method 700 begins with the computer obtaining 710 a plan for insertion of the implant. The plan may include a 3D model of the target in which the implant will be inserted as well as the desired entry point and insertion trajectory for the implant. For example the plan may be loaded from a USB drive or other computer-readable medium.

The computer receives 720 selection of registration points on the surface of the target. Typically, the operator (e.g., a surgeon) will select registration points that are likely to be easy to identify on the real surface (e.g., the glenoid surface) that is represented by the 3D model. The operator may select the registration points in advance as part of a pre-planning process or at the time the implant is to be inserted (e.g., as part of a surgical procedure). Regardless of how the registration points are selected, the computer guides 730 the operator to register the tool by aligning one or more contact regions of the tool with the selected registration points. For example, in the case of a three-point finder probe, the computer may prompt the operator to place the three prongs of the probe at three corresponding registration points on the surface.

Once the initial registration has been conducted (e.g., after the operator has provided user input indicating that the contact regions are aligned with the registration points), the computer may prompt 740 the operator to confirm the accuracy of the registration. For example, the computer may identify a set of validation points, at least some of which are different from the registration points, and direct the operator to align the contact regions of the tool with the validation points. If the registration was successful, the location and orientation of the tool when aligned with the validation points will match the location and orientation of a virtual representation of the tool displayed in conjunction with the 3D model.

The computer guides 750 the operator to place the tip of the implant at the insertion location. In the case of a three-point finder probe, the operator may be directed to use one of the contact regions as a pivot point and orient the tool to a predetermined orientation that aligns a channel or guide of the tool with the entry location. Typically the vertex point of the three-point finder is used as the pivot point, but any of the contact regions may be used. The computer can provide a user interface to guide the operator to align the tool correctly to identify the entry location (e.g., the user interfaces shown in FIGS. 5E through 5H). Once the tool is aligned with the entry location, the operator may push the implant through the channel or guide until it contacts the surface at the entry location. Alternatively, the tool used for registration may include a laser or other marker that identifies the insertion location when the tool is correctly aligned and enables the operator to place the tip of the implant at that location using another tool.

The computer guides 760 the operator to align the implant at the desired insertion angle. As described previously, a single tool may be used for registration and alignment. In which case, the computer provides a user interface that guides 760 the operator to move the tool using the tip of the implant (that is placed at the entry location) as a pivot point until the implant is aligned with the desired insertion trajectory and then insert the implant. Alternatively, if a separate tool is used for insertion, the operator may mark the insertion location and then position, align, and insert the implant using the insertion tool. In either case, the computer may provide a user interface (e.g., the user interfaces shown in FIGS. 5I through 5L) to guide 760 the operator to position the tool correctly such that the implant is aligned with the desired insertion trajectory.

In some embodiments, the computer receives user input from the operator confirming 770 insertion of the implant, which can trigger follow up steps, such as prompting the operator to confirm the implant was inserted correctly, etc.

FIG. 8 illustrates one embodiment of a method 800 for inserting an implant using a tool with computer-aided navigation. In the embodiment shown, the method 800 begins with the operator identifying 810 registration points on the target surface. A computer may display a set of registration points on a virtual representation of the target surface. The operator identifies 810 the corresponding points on the actual surface and aligns 820 one or more contact regions of the tool with the registration points on the target surface.

The operator may verify 830 the accuracy of the registration (as described previously) and place 840 the tip of the implant at the marked insertion location. The insertion location may be marked digitally on the virtual representation of the target surface, physically on the target surface (e.g., using a Bovie or laser pointer), or both. The operator aligns 850 the implant at an indicated angle such that the implant will enter the surface at a desired trajectory. As described previously, the operator may be guided to place 840 the tip at the correct location and align 850 the implant with the desired trajectory by a user interface provided by the computer. Once the operator is satisfied that the implant is at the correct location and has the desired alignment, the operator may insert 860 the implant (e.g., by using the same or a different tool to drill the implant into the surface).

Example Machine Architecture

Figure 9:
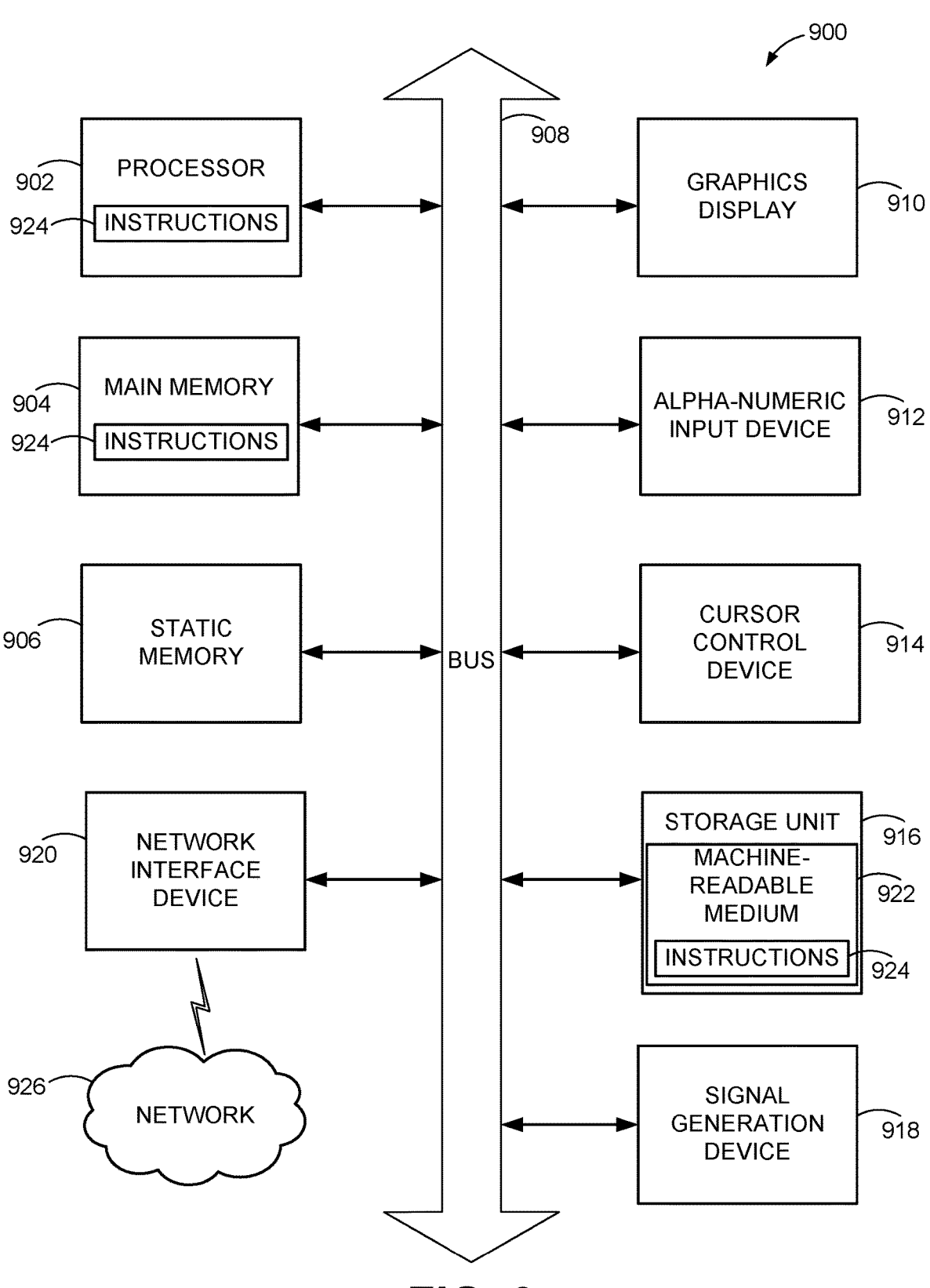
FIG. 9 is a block diagram of an example of a computer suitable for use with the surgical tool, according to one embodiment.

FIG. 9 is a block diagram illustrating components of an example machine able to read instructions from a machine-readable medium and execute them in a processor (or controller). Specifically, FIG. 9 shows a diagrammatic representation of a machine in the example form of a computer system 900. The computer system 900 can be used to execute instructions 924 (e.g., program code or software) for causing the machine to perform any one or more of the methodologies (or processes) described herein. In alternative embodiments, the machine operates as a standalone device or a connected (e.g., networked) device that connects to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a smartphone, an internet of things (IoT) appliance, a network router, switch or bridge, or any machine capable of executing instructions 924 (sequential or otherwise) that specify actions to be taken by that machine. Further, while only a single machine is illustrated, the term "machine" shall also be taken to include any collection of machines that individually or jointly execute instructions 924 to perform any one or more of the methodologies discussed herein.

The example computer system 900 includes one or more processing units (generally processor 902). The processor 902 is, for example, a central processing unit (CPU), a graphics processing unit (GPU), a digital signal processor (DSP), a controller, a state machine, one or more application specific integrated circuits (ASICs), one or more radio-frequency integrated circuits (RFICs), or any combination of these. The computer system 900 also includes a main memory 904. The computer system may include a storage unit 916. The processor 902, memory 904 and the storage unit 916 communicate via a bus 908.

In addition, the computer system 906 can include a static memory 906, a display driver 910 (e.g., to drive a plasma display panel (PDP), a liquid crystal display (LCD), or a projector). The computer system 900 may also include alphanumeric input device 912 (e.g., a keyboard), a cursor control device 914 (e.g., a mouse, a trackball, a joystick, a motion sensor, or other pointing instrument), a signal generation device 918 (e.g., a speaker), and a network interface device 920, which also are configured to communicate via the bus 908.

The storage unit 916 includes a machine-readable medium 922 on which is stored instructions 924 (e.g., software) embodying any one or more of the methodologies or functions described herein. The instructions 924 may also reside, completely or at least partially, within the main memory 904 or within the processor 902 (e.g., within a processor's cache memory) during execution thereof by the computer system 900, the main memory 904 and the processor 902 also constituting machine-readable media. The instructions 924 may be transmitted or received over a network 926 via the network interface device 920.

While machine-readable medium 922 is shown in an example embodiment to be a single medium, the term "machine-readable medium" should be taken to include a single medium or multiple media (e.g., a centralized or distributed database, or associated caches and servers) able to store the instructions 924. The term "machine-readable medium" shall also be taken to include any medium that is capable of storing instructions 924 for execution by the machine and that cause the machine to perform any one or more of the methodologies disclosed herein. The term "machine-readable medium" includes, but not be limited to, data repositories in the form of solid-state memories, optical media, and magnetic media.

Additional Considerations

Some portions of above description describe the embodiments in terms of algorithmic processes or operations. These algorithmic descriptions and representations are commonly used by those skilled in the computing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Similarly, use of "a" or "an" preceding an element or component is done merely for convenience. This description should be understood to mean that one or more of the elements or components are present unless it is obvious that it is meant otherwise.

Where values are described as "approximate" or "substantially" (or their derivatives), such values should be construed as accurate +/−10% unless another meaning is apparent from the context. From example, "approximately ten" should be understood to mean "in a range from nine to eleven."

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Upon reading this disclosure, those of skill in the art will appreciate still additional alternative structural and functional designs for a tool and a processes for inserting an implant into a surface at a desired location and with a desired trajectory. Thus, while particular embodiments and applications have been illustrated and described, it is to be understood that the described subject matter is not limited to the precise construction and components disclosed. The scope of protection should be limited only by the following claims.

What is claimed is:

1. A tool for inserting an implant in a target surface at a desired location and angle, the tool comprising:

a sensor unit configured to generate position data indicating a position of a body of the tool, wherein the sensor unit comprises a mount for physically connecting a probe to the sensor unit, the body further comprising a power unit configured to connect to the sensor unit and provide power to one or more sensors of the sensor unit, wherein the power unit comprises one or more controls on an exterior surface of the power unit, wherein the one or more controls comprise one or more buttons configured to receive an input;

the probe including:

an attachment portion that attaches the probe to the body;

a head, coupled to the attachment portion, having a plurality of contact portions configured to contact the target surface, wherein the head is coupled to the attachment portion of the probe via a shaft; and a connector at a proximal end of the shaft, wherein the connector is configured to connect the probe to the mount; and a controller configured to send orientation data to a computer, wherein the computer is configured to provide assistance to a user in positioning the tool to insert the implant at the desired location and/or angle, wherein the controller comprises a printed circuit board assembly, wherein the printed circuit board assembly is inside the power unit.

2. The tool of claim 1, wherein the position data is orientation data that indicates an orientation of the body.

3. The tool of claim 1, wherein the probe further comprises a channel having a central axis, wherein the channel is configured to receive the implant and align a longitudinal axis of the implant with the central axis, and wherein the channel is mounted to the shaft between the proximal end of the shaft and a distal end of the shaft.

4. The tool of claim 3, wherein the probe comprises at least one additional channel, each additional channel having a corresponding additional central axis that is different from the central axis of the channel.

5. The tool of claim 1, wherein the power unit is disposable and the sensor unit is reusable.

6. The tool of claim 1, wherein the contact portions include a tip of a first prong and a tip of a second prong.

7. The tool of claim 6, wherein a distance between the tip of the first prong and the tip of the second prong is configurable.

8. The tool of claim 1, wherein the contact portions are parts of a planar surface configured to be placed such that a plurality of contact portions of the planar surface contact the target surface during a registration process.

9. The tool of claim 1, wherein the head includes a T-shaped jig having adjustable portions configured to grip a periphery of the target surface along at least two axes.

10. The tool of claim 1, wherein the surface is of a bone and the implant is a surgical wire.

11. The tool of claim 1, wherein the one or more controls further comprises one or more indicators configured to convey information to the user.

12. The tool of claim 1, wherein the printed circuit board assembly is configured to receive signals from the one or more controls.

13. The tool of claim 1, wherein the printed circuit board assembly is configured to receive data from the computer.

14. The tool of claim 1, wherein the controller further comprises a sensor unit printed circuit board assembly, wherein the sensor unit printed circuit board assembly is inside the sensor unit, wherein the one or more sensors are mounted on the sensor unit printed circuit board assembly.

15. The tool of claim 1, wherein the probe further comprises a channel having a central axis, wherein the channel is configured to receive the implant and align a longitudinal axis of the implant with the central axis, wherein the contact portion includes a tip of a first prong and a tip of a second prong, and wherein the implant is configured to extend between the tip of the first prong and the tip of the second prong.

* * * * *